(12) United States Patent
Jin

(10) Patent No.: US 9,987,298 B2
(45) Date of Patent: Jun. 5, 2018

(54) APTAMER FOR FGF2 AND USE THEREOF

(71) Applicant: RIBOMIC INC., Tokyo (JP)

(72) Inventor: Ling Jin, Tokyo (JP)

(73) Assignee: RIBOMIC INC., Tokyo (JP)

( * ) Notice: Subject to any disclaimer, the term of this patent is extended or adjusted under 35 U.S.C. 154(b) by 0 days. days.

(21) Appl. No.: 15/128,495

(22) PCT Filed: Mar. 24, 2015

(86) PCT No.: PCT/JP2015/058992
§ 371 (c)(1),
(2) Date: Sep. 23, 2016

(87) PCT Pub. No.: WO2015/147017
PCT Pub. Date: Oct. 1, 2015

(65) Prior Publication Data
US 2017/0157165 A1    Jun. 8, 2017

(30) Foreign Application Priority Data

Mar. 24, 2014  (JP) ................. 2014-060966

(51) Int. Cl.
*A61K 31/712* (2006.01)
*C07H 21/02* (2006.01)
*C07H 21/04* (2006.01)

(52) U.S. Cl.
CPC ........... *A61K 31/712* (2013.01); *C07H 21/02* (2013.01); *C07H 21/04* (2013.01); *A61K 2121/00* (2013.01)

(58) Field of Classification Search
CPC ....... A61K 31/712; C07H 21/02; C07H 21/04
See application file for complete search history.

(56) References Cited

U.S. PATENT DOCUMENTS

| 7,795,419 | B2 * | 9/2010 | Bentwich | ............... | C12N 15/111 |
| | | | | | 536/24.32 |
| 2013/0039855 | A1 * | 2/2013 | Nakamura | ......... | A61K 31/7105 |
| | | | | | 424/9.1 |

FOREIGN PATENT DOCUMENTS

| WO | 91/19813 | 12/1991 |
| WO | 94/08050 | 4/1994 |
| WO | 95/07364 | 3/1995 |
| WO | 2013/186857 | 12/2013 |

OTHER PUBLICATIONS

Hisataka Yasuda et al., "Osteoclast differentiation factor is a ligand for osteoprotegerin/osteoclastogenesis-inhibitory factor and is identical to TRANCE/RANKL", Proceedings of the National Academy of Sciences, vol. 95, 1998, pp. 3597-3602.
Akihisa Yamashita et al., "Fibroblast Growth Factor-2 Determines Severity of Joint Disease in Adjuvant-Induced Arthritis in Rats", The Journal of Immunology, vol. 168, 2002, pp. 450-457.
Kazuki Yano et al., "Synovial cells from a patient with rheumatoid arthritis produce osteoclastogenesis inhibitory factor/osteoprotegerin: reciprocal regulation of the production by inflammatory cytokines ad basic fibroblast growth factor", J Bone Miner Metab, 2001, vol. 19, pp. 365-372.
Jennifer L. Roccisana et al., "Functional Role for Heat Shock Factors in the Transcriptional Regulation of Human RANK Ligand Gene Expression in Stromal/Osteoblast Cells", The Journal of Biological Chemistry, vol. 279, No. 11, 2004, pp. 10500-10507.
N. Manabe et al., "Involvement of fibroblast growth factor-2 in joint destruction of rheumatoid arthritis patients", Rheumatology, vol. 38, 1999, pp. 714-720.
Jamie J. Cannone et al., "Crystallization of bFGF-DNA aptamer complexes using a Sparse Matrix designed for protein-nucleic acid complexes", Journal of Crystal Growth, vol. 232, 2001, pp. 409-417.
A. Ishiguro et al., "In vivo analysis of FGF2 in murine model of rheumatoid arthritis by RNA aptamer", 14th RNA Meeting in Tohoku Yoshishu, 2012, pp. 60, cited in ISR.
International Search Report dated Jun. 30, 2015 in corresponding International (PCT) Application No. PCT/JP2015/058992.

* cited by examiner

*Primary Examiner* — Kevin K Hill
(74) *Attorney, Agent, or Firm* — Wenderoth, Lind & Ponack, L.L.P.

(57) ABSTRACT

Provided by the present invention are an aptamer having an inhibitory activity on FGF2; a complex containing an aptamer having a binding activity or an inhibitory activity on FGF2, and a functional substance (e.g., affinity substance, labeling substance, enzyme, drug delivery vehicle, or drug and the like); a medicament, diagnostic reagent or labeling agent containing an aptamer having a binding activity or an inhibitory activity on FGF2, or a complex containing said aptamer and a functional substance; and the like.

11 Claims, 3 Drawing Sheets

```
                        SEQUENCE LISTING

<160> NUMBER OF SEQ ID NOS: 21

<210> SEQ ID NO 1
<211> LENGTH: 38
<212> TYPE: RNA
<213> ORGANISM: Artificial Sequence
<220> FEATURE:
<223> OTHER INFORMATION: Aptamer against FGF2

<400> SEQUENCE: 1
gggauacuag ggcauuaaug uuaccagugu agucucga                              38

<210> SEQ ID NO 2
<211> LENGTH: 37
<212> TYPE: RNA
<213> ORGANISM: Artificial Sequence
<220> FEATURE:
<223> OTHER INFORMATION: Aptamer against FGF2

<400> SEQUENCE: 2
gggaaacuag ggcguuaacg ugaccagugu uucucga                               37

<210> SEQ ID NO 3
<211> LENGTH: 36
<212> TYPE: RNA
<213> ORGANISM: Artificial Sequence
<220> FEATURE:
<223> OTHER INFORMATION: Aptamer against FGF2

<400> SEQUENCE: 3
gggauacuag ggcauuaaug uuaccagugu aguccc                                36

<210> SEQ ID NO 4
<211> LENGTH: 34
<212> TYPE: RNA
<213> ORGANISM: Artificial Sequence
<220> FEATURE:
<223> OTHER INFORMATION: Aptamer against FGF2

<400> SEQUENCE: 4
ggauacuagg gcauuaaugu uaccagugua gucc                                  34

<210> SEQ ID NO 5
<211> LENGTH: 38
<212> TYPE: RNA
<213> ORGANISM: Artificial Sequence
<220> FEATURE:
<223> OTHER INFORMATION: Aptamer against FGF2

<400> SEQUENCE: 5
ggggauacua gggcauuaau guuaccagug uagucccc                              38

<210> SEQ ID NO 6
```

<211> LENGTH: 37
<212> TYPE: RNA
<213> ORGANISM: Artificial Sequence
<220> FEATURE:
<223> OTHER INFORMATION: Aptamer against FGF2

<400> SEQUENCE: 6
agggauacua gggcauuaau guuaccagug uagcccc                              37

<210> SEQ ID NO 7
<211> LENGTH: 35
<212> TYPE: RNA
<213> ORGANISM: Artificial Sequence
<220> FEATURE:
<223> OTHER INFORMATION: Aptamer against FGF2

<400> SEQUENCE: 7
gggaaacuag ggcguuaacg ugaccagugu uuccc                                35

<210> SEQ ID NO 8
<211> LENGTH: 36
<212> TYPE: RNA
<213> ORGANISM: Artificial Sequence
<220> FEATURE:
<223> OTHER INFORMATION: Aptamer against FGF2

<400> SEQUENCE: 8
cggauacuag ggcauuaaug uuaccagugu aguccg                               36

<210> SEQ ID NO 9
<211> LENGTH: 36
<212> TYPE: RNA
<213> ORGANISM: Artificial Sequence
<220> FEATURE:
<223> OTHER INFORMATION: Aptamer against FGF2

<400> SEQUENCE: 9
ccgauacuag ggcauuaaug uuaccagugu agucgg                               36

<210> SEQ ID NO 10
<211> LENGTH: 36
<212> TYPE: RNA
<213> ORGANISM: Artificial Sequence
<220> FEATURE:
<223> OTHER INFORMATION: Aptamer against FGF2

<400> SEQUENCE: 10
gggauacuag ggcguuaacg uuaccagugu aguccc                               36

<210> SEQ ID NO 11
<211> LENGTH: 36
<212> TYPE: RNA
<213> ORGANISM: Artificial Sequence
<220> FEATURE:
<223> OTHER INFORMATION: Aptamer against FGF2

<400> SEQUENCE: 11
gggauacuag ggccuuaagg uuaccagugu aguccc                               36

<210> SEQ ID NO 12
<211> LENGTH: 36
<212> TYPE: RNA
<213> ORGANISM: Artificial Sequence
<220> FEATURE:
<223> OTHER INFORMATION: Aptamer against FGF2

<400> SEQUENCE: 12
gggauacuag ggcauuuaug uuaccagugu aguccc                               36

<210> SEQ ID NO 13
<211> LENGTH: 72
<212> TYPE: DNA
<213> ORGANISM: Artificial Sequence
<220> FEATURE:
<223> OTHER INFORMATION: Template DNA
<220> FEATURE:
<221> NAME/KEY: misc_feature
<222> LOCATION: (6)..(35)
<223> OTHER INFORMATION: Each "n" independently stands for a, g, t or c.

<400> SEQUENCE: 13
tcgagnnnnn nnnnnnnnnn nnnnnnnnnn nnnnntccct atagtgagtc gtattagcag      60
ctccacaggc tt                                                         72

<210> SEQ ID NO 14
<211> LENGTH: 17
<212> TYPE: RNA
<213> ORGANISM: Artificial Sequence
<220> FEATURE:
<223> OTHER INFORMATION: Forward ligate

<400> SEQUENCE: 14
uaauacgacu cacuaua                                                    17

<210> SEQ ID NO 15
<211> LENGTH: 37
<212> TYPE: DNA
<213> ORGANISM: Artificial Sequence
<220> FEATURE:
<223> OTHER INFORMATION: Forward primer

<400> SEQUENCE: 15
aagcctgtgg agctgctaat acgactcact ataggga                              37

<210> SEQ ID NO 16
<211> LENGTH: 21
<212> TYPE: DNA
<213> ORGANISM: Artificial Sequence
<220> FEATURE:
<223> OTHER INFORMATION: Forward bridge

<400> SEQUENCE: 16
tccctatagt gagtcgtatt a                                               21

<210> SEQ ID NO 17
<211> LENGTH: 25
<212> TYPE: DNA
<213> ORGANISM: Artificial Sequence
<220> FEATURE:
<223> OTHER INFORMATION: Reverse bridge

<400> SEQUENCE: 17
tcttgttcag cttagttctc tcgag                                           25

<210> SEQ ID NO 18
<211> LENGTH: 20
<212> TYPE: DNA
<213> ORGANISM: Artificial Sequence
<220> FEATURE:
<223> OTHER INFORMATION: Reverse ligate

<400> SEQUENCE: 18

```
gagaactaag ctgaacaaga                                          20

<210> SEQ ID NO 19
<211> LENGTH: 31
<212> TYPE: RNA
<213> ORGANISM: Artificial Sequence
<220> FEATURE:
<223> OTHER INFORMATION: Aptamer against FGF2
<220> FEATURE:
<221> NAME/KEY: misc_feature
<222> LOCATION: (1)..(1)
<223> OTHER INFORMATION: n is 0 or more bases and each is a, g, u, or c
<220> FEATURE:
<221> NAME/KEY: misc_feature
<222> LOCATION: (5)..(5)
<223> OTHER INFORMATION: n is a, g, u, or c
<220> FEATURE:
<221> NAME/KEY: misc_feature
<222> LOCATION: (14)..(14)
<223> OTHER INFORMATION: n is a, g, u, or c
<220> FEATURE:
<221> NAME/KEY: misc_feature
<222> LOCATION: (19)..(19)
<223> OTHER INFORMATION: n is a, g, u, or c
<220> FEATURE:
<221> NAME/KEY: misc_feature
<222> LOCATION: (22)..(22)
<223> OTHER INFORMATION: n is a, g, u, or c
<220> FEATURE:
<221> NAME/KEY: misc_feature
<222> LOCATION: (31)..(31)
<223> OTHER INFORMATION: n is 0 or more bases and each is a, g, u, or c

<400> SEQUENCE: 19
ngganacuag ggcnuuaang unaccagugu n                             31

<210> SEQ ID NO 20
<211> LENGTH: 34
<212> TYPE: RNA
<213> ORGANISM: Artificial Sequence
<220> FEATURE:
<223> OTHER INFORMATION: Aptamer against FGF2
<220> FEATURE:
<221> NAME/KEY: misc_feature
<222> LOCATION: (34)..(34)
<223> OTHER INFORMATION: n is 0 or more bases and each is a, g, u, or c

<400> SEQUENCE: 20
gggaaacuag ggcguuaacg ugaccagugu uucn                          34

<210> SEQ ID NO 21
<211> LENGTH: 35
<212> TYPE: RNA
<213> ORGANISM: Artificial Sequence
<220> FEATURE:
<223> OTHER INFORMATION: Aptamer against FGF2
<220> FEATURE:
<221> NAME/KEY: misc_feature
<222> LOCATION: (1)..(1)
<223> OTHER INFORMATION: n is 0 or more bases and each is a, g, u, or c
<220> FEATURE:
<221> NAME/KEY: misc_feature
<222> LOCATION: (35)..(35)
<223> OTHER INFORMATION: n is 0 or more bases and each is a, g, u, or c

<400> SEQUENCE: 21
nggauacuag ggcauuaaug uuaccagugu agucn                         35
```

APTAMER FOR FGF2 AND USE THEREOF

TECHNICAL FIELD

The present invention relates to an aptamer for FGF2, a method of utilizing the same, and the like.

BACKGROUND ART

Basic fibroblast growth factor (FGF2 or bFGF) is a growth factor secreted from various cells, which is deeply involved in the cell proliferation and differentiation in developmental stages and shows high expression during tissue repair and in cancer tissues in adults.

While human FGF2 has plural isoforms, only an isoform having the lowest molecular weight is extracellularly secreted. This isoform is an about 18 kDa protein consisting of 154 amino acids, which is free of a sugar chain and has a basic isoelectric point of 9.4. While the function of high molecular weight isoforms (22, 22.5, 24, 34 kD) of FGF2 with different open reading frames is not clear as yet, they are considered to have a nuclear localization signal and function in the nucleus.

The human FGF family protein is known to include 22 kinds from FGF1 to FGF23 (FGF15 and FGF19 are now unified as FGF19 since they are the same molecules). By phylogenetic analysis, FGF2 is classified into FGF1 sub-family together with FGF1. The homology of amino acid sequence with FGF1 is the highest of all FGFs, and its value is 55%. FGF receptor (FGFR) is a receptor tyrosine kinase and classified into 4 subtypes. Each of FGFR1-3 is known to include b and c isoforms. FGF2 binds to FGFR1b, FGFR1c, FGFR2c and FGFR3c, and FGFR4 therefrom to dimerize these receptors.

Mouse fibroblast (NIH-3T3 cell) expresses FGFR1 on the cellular membrane surface. FGFR1 is known to be activated when bound to human FGF2. When FGF2 is bound to FGFR1, MAP kinase (mitogen-activated protein kinase) pathway, PIK3 (phosphatidylinositol 3-kinase)/AKT1 (protein kinase B) pathway and the like are activated via FRS2 (Fibroblast growth factor receptor substrate 2), Grb2 (growth factor receptor-bound protein 2), SOS, and finally, expression of various cytokine and receptor genes such as VEGF (vascular endothelial growth factor precursor)-A, VEGF-C, HGF (hepatocyte growth factor), angiopoietin-2, VEGFR, PDGFR-α (platelet-derived growth factor beta receptor-α) and the like is induced.

FGF2 has a heparin binding region and, like other FGFs, is bound to heparin and heparan sulfate. It is generally considered that FGF2 secreted from a cell is bound to a heparan sulfate of an extracellular matrix, concentrated, and protected from protease. To function as a ligand, FGF2 needs to be liberated from the extracellular matrix bound thereto, in which FGF-BP (FGF-binding protein) is reported to be involved to aid induction to FGFR.

FGF2 is known to have a strong growth, cell migration-promoting effect for vascular endothelial cells, and be deeply involved in the angiogenesis of tumor tissues. A particularly high FGF2 serum concentration in tumor with many blood vessels, for example, renal cancer and the like, has been reported, and FGF2 is present in various other tumors such as prostate cancer, breast cancer, lung cancer and the like.

Factors such as FGF1, VEGF, TNF-α (tumor necrosis factor-α), PDGF, EGF (epidermal growth factor), MMP (matrix metallopeptidase), angiogenin and the like are involved in angiogenesis besides FGF2. These factors are secreted from tumor, angioblastic cells, supporting cells and the like, and contribute to angiogenesis as growth factors of autocrine or paracrine. However, FGF2 is different from other factors since it acts not only on vascular endothelial cells but also mesenchymal cells surrounding the endothelial cells, such as smooth muscle cell and the like. In other words, it is considered that FGF2 stimulates mesenchymal cell to promote expression of PDGF, PDGFR, VEGF, HGF and the like, and these factors enhance direct growth of vascular endothelial cells.

At present, many attempts have been made to develop a drug that inhibits abnormal angiogenesis in a tumor tissue to block a nutrient supply pathway to a tumor tissue. There is a drug actually used in clinical situations such as a humanized anti-VEGF monoclonal antibody (avastin (registered trade mark)) developed by Genentech, which has been confirmed to show an effect for colon cancer and non-small cell lung cancer. However, a strong antitumor drug has not been developed yet. Many of these drugs target VEGF and PDGF, and are expected to block the initial stages of abnormal angiogenesis by targeting FGF2 that functions at more upstream.

Abnormal angiogenesis is also involved in, besides tumor, diseases such as chronic inflammations (e.g., periodontal disease, scleroderma, neovascular glaucoma, arthritis and the like), psoriasis, age-related macular degeneration and the like.

On the other hand, an attempt has been made to use the strong angiogenic action of FGF2 for the treatment of occlusive vascular disorders and wound healing. In fact, the human FGF2 preparation (FIBLAST (registered trade mark) Spray) of Kaken Pharmaceutical Co., Ltd. has already been approved and sold as a drug for promoting wound healing.

While FGF2 is known to have an osteogenesis promoting effect, it is also attracting attention as a bone resorption-promoting factor since it is involved in articular destruction in chronic rheumatoid arthritis patients. In chronic rheumatoid arthritis characterized by autoimmune arthritis, the number of osteoclasts increases to promote bone resorption, which in turn progresses bone destruction.

FGF2 stimulates mesenchymal cell to promote expression of inflammatory cytokines and growth factors such as PDGF, PDGFR, VEGF, HGF and the like, as well as promotes angiogenesis and induces bone destruction. It has been clarified that FGF2 is a key molecule involved in significant pathology in chronic rheumatoid arthritis (non-patent document 1).

Osteoprotegerin (OPG) is a decoy receptor of an osteoclast inducer, RANKL, and is known to antagonize RANK and suppress differentiation induction into osteoclast and the function thereof (non-patent document 2). OPG produced from synovial cell is also known to be suppressed by stimulation of FGF2 (non-patent document 3). Furthermore, FGF2 encourages coupling of osteoblasts and osteoclast precursor cells by inducing high expression of RANKL by osteoblasts, as a result of which promotes differentiation into osteoclast and activation (non-patent document 4).

Once the function of FGF2 can be controlled, the effect as a therapeutic drug for articular destruction via activation of osteoclast should be sufficiently expected. In fact, direct articular administration of an anti-FGF2 neutralizing antibody to AIA model rats is known to mitigate the symptom. However, a suppressive effect on the onset thereof is small, and particularly, a healing effect by the administration after the onset has not been confirmed (non-patent document 5).

In recent years, applications of RNA aptamers to medicaments, diagnostic reagents, and test reagents have been drawing attention; some RNA aptamers have already been in clinical study stage or in practical use. In December 2004, the world's first RNA aptamer drug, Macugen, was approved as a therapeutic drug for age-related macular degeneration in the US. An RNA aptamer refers to an RNA that binds specifically to a target substance such as a protein, and can be prepared using the SELEX (Systematic Evolution of Ligands by Exponential Enrichment) method (see Patent documents 1-3). In the SELEX method, an RNA that binds specifically to a target substance is selected from an RNA pool with about $10^{14}$ different nucleotide sequences. The RNA structure used has a random sequence of about 40 residues, which is flanked by primer sequences. This RNA pool is allowed to be assembled with a target substance, and only the RNA that has bound to the target substance is collected using a filter and the like. The RNA collected is amplified by RT-PCR, and this is used as a template for the next round. By repeating this operation about 10 times, an RNA aptamer that binds specifically to the target substance can sometimes be acquired.

Patent document 4 describes an aptamer that binds to FGF2, which is obtained by the above-mentioned SELEX method. However, the sequences of the aptamers are different from those of the aptamers specifically shown in the present specification. In addition, this document does not suggest the aptamers specifically shown in the present specification.

DOCUMENT LIST

Patent Documents patent document 1: WO 91/19813
patent document 2: WO 94/08050
patent document 3: WO 95/07364
patent document 4: WO 2011/099576

Non-Patent Documents non-patent document 1: Manabe N. et al. Reumatology. 1999; 38; 714-720
non-patent document 2: Yasuda H. et al. Proc. Natl. Acad. Sci USA. 1998; 95; 3597-3602
non-patent document 3: Yano K. et al. J. Bone Miner Metab. 2001; 19; 365-372
non-patent document 4: Roccisana J L et al. J. Biol. Chem. 279: 10500-10507 (2004)
non-patent document 5: Yamashita A. et al. J. Immunol. 2002; 168; 450-457

SUMMARY OF THE INVENTION

Problems to be Solved by the Invention

The present invention is directed to providing an aptamer for FGF2 and a method of utilizing the same, and the like.

Means of Solving the Problems

The present inventors investigated diligently to solve the problem described above and succeeded in preparing an aptamer of good quality for FGF2, which resulted in the completion of the present invention.

Accordingly, the present invention is as follows.

[1] An aptamer that binds to FGF2, which comprises a nucleotide sequence represented by the following formula (1) (wherein uracil is optionally thymine), and which is the following (a) or (b):

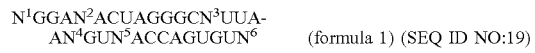
(formula 1) (SEQ ID NO:19)

$N^1$ and $N^6$ are each independently any 0 to several bases, $N^2$, $N^3$, $N^4$ and $N^5$ are independently any one base,
(a) an aptamer wherein, in the nucleotides contained in the aptamer,
  (i) the 2'-position of the ribose of each pyrimidine nucleotide is a fluorine atom,
  (ii) the 2'-position of the ribose of each purine nucleotide is a hydroxy group;
(b) the aptamer of (a), wherein
  (i) the fluorine atom at the 2'-position of the ribose of each pyrimidine nucleotide is independently unsubstituted, or substituted by an atom or group selected from the group consisting of a hydrogen atom, a hydroxy group and a methoxy group,
  (ii) the hydroxy group at the 2'-position of the ribose of each purine nucleotide is independently unsubstituted, or substituted by an atom or group selected from the group consisting of a hydrogen atom, a methoxy group and a fluorine atom.

[2] The aptamer of [1], wherein
$N^1$ is G, GG, AG, C or gap,
$N^2$ is A or U,
$N^3$ is G, C or A, n may be 0 or more bases and can be a, g, u, or c
$N^4$ is G, C or U,
$N^5$ is G or U, and
$N^6$ is $UUCN^{61}$ or $AGUCN^{62}$ wherein $N^{61}$ and $N^{62}$ are each independently any 0 to several bases.

[3] The aptamer of [1] or [2], comprising a nucleotide sequence represented by the following formula (2) or (3):

(formula 2) (SEQ ID NO:20)

(formula 3) (SEQ ID NO:21).

[4] The aptamer of any of [1]-[3], comprising a nucleotide sequence shown in SEQ ID NO: 2 or 7.
[5] The aptamer of any of [1]-[3], comprising a nucleotide sequence shown in SEQ ID NO: 1, 3, 4, 5, 6, 8, 10 or 11.
[6] The aptamer of any of [1]-[5], wherein 1 or several nucleotides are substituted, deleted, inserted or added, which is
(a) an aptamer wherein, in the nucleotides contained in the aptamer,
  (i) the 2'-position of ribose of each pyrimidine nucleotide is a fluorine atom,
  (ii) the 2'-position of the ribose of each purine nucleotide is a hydroxy group;
(b) the aptamer of (a), wherein
  (i) the fluorine atom at the 2'-position of the ribose of each pyrimidine nucleotide is independently unsubstituted, or substituted by an atom or group selected from the group consisting of a hydrogen atom, a hydroxy group and a methoxy group,
  (ii) the hydroxy group at the 2'-position of the ribose of each purine nucleotide is independently unsubstituted, or substituted by an atom or group selected from the group consisting of a hydrogen atom, a methoxy group and a fluorine atom.
[7] The aptamer of any of [1]-[6], which has a nucleotide length of not more than 45.
[8] The aptamer of any of [1]-[7], which inhibits binding of FGF2 and an FGF receptor.
[9] The aptamer of any of [1]-[8], wherein at least one nucleotide is modified.

[10] A complex comprising the aptamer of any one of [1] to [9] and a functional substance.
[11] The complex of [10], wherein the functional substance is an affinity substance, a labeling substance, an enzyme, a drug delivery vehicle or a drug.
[12] A medicament comprising the aptamer of any one of [1] to [9] or the complex of [10] or [11].
[13] A medicament for the treatment or prophylaxis of a disease accompanied by angiogenesis, bone-articular disease or pain, comprising the aptamer of any of [1]-[9] or the complex of [10] or [11].
[14] A method for the treatment or prophylaxis of a disease accompanied by angiogenesis, bone-articular disease or pain, comprising administering an effective amount of the aptamer of any of [1]-[9] or the complex of [10] or [11] to a subject.
[15] The aptamer of any of [1]-[9] or the complex of [10] or [11], for use for the treatment or prophylaxis of a disease accompanied by angiogenesis, bone-articular disease or pain.
[16] Use of the aptamer of any of [1]-[9] or the complex of [10] or [11], in the production of a medicament for the treatment or prophylaxis of a disease accompanied by angiogenesis, bone-articular disease or pain.

Effect of the Invention

The aptamer and the complex of the present invention can be useful as therapeutic or prophylactic drugs, diagnostic reagents or reagents for a disease accompanied by angiogenesis, bone-articular disease or pain. The aptamer and the complex of the present invention can also be useful for the purification and concentration of FGF2, labeling of FGF2 as well as detection and quantification of FGF2.

DESCRIPTION OF EMBODIMENTS

Figure 1:
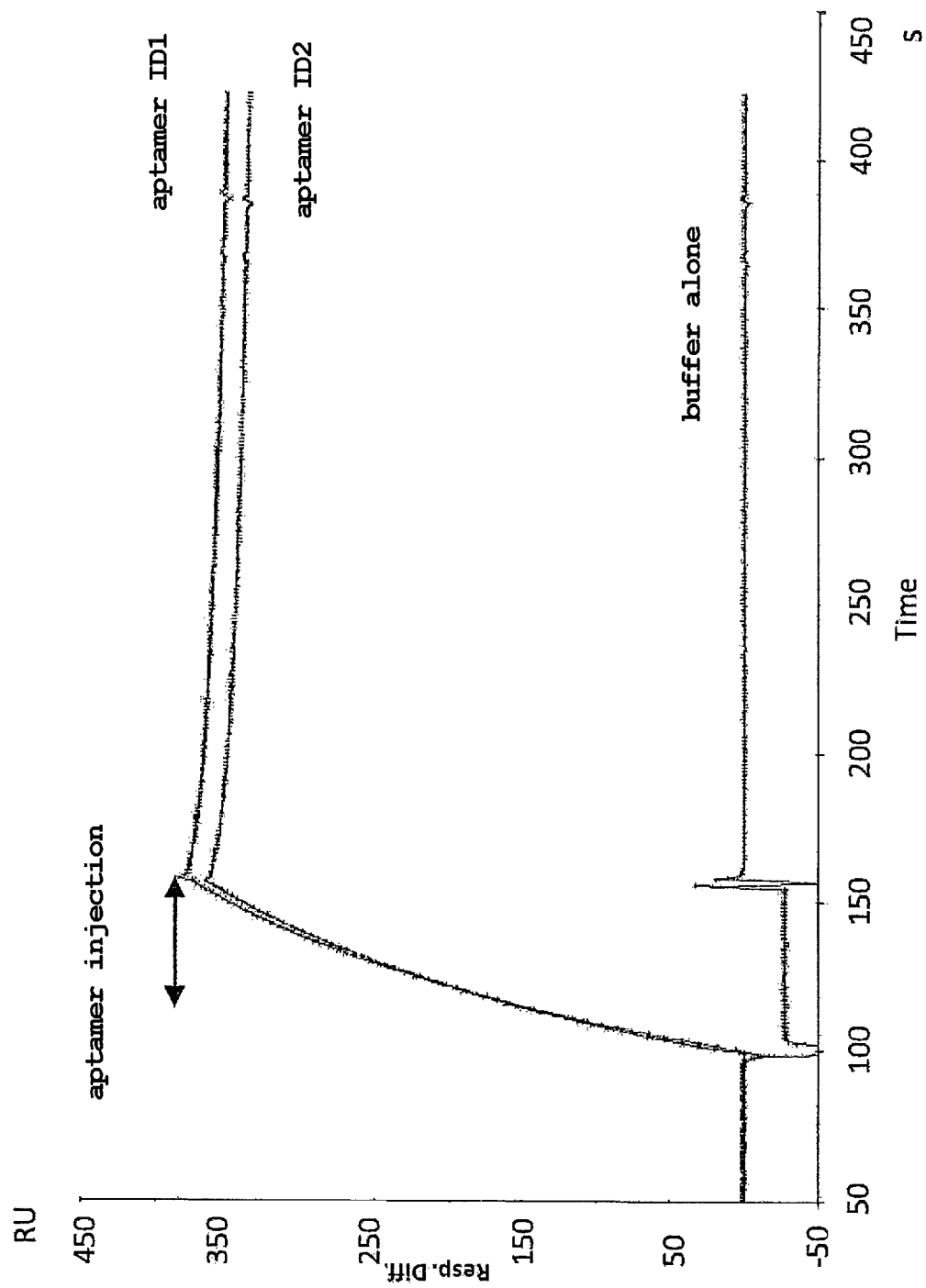
FIG. 1 is a sensorgram showing that aptamers shown by aptamer IDs 1 and 2 bind to human FGF2.

In one embodiment, the present invention provides an aptamer that binds to FGF2, which comprises a nucleotide sequence represented by the following formula (1) (wherein uracil is optionally thymine), and which is the following (a) or (b):

(formula 1) (SEQ ID NO:19)

$N^1$ and $N^6$ are each independently any 0 to several bases, $N^2$, $N^3$, $N^4$ and $N^5$ are independently any one base,
(a) an aptamer wherein, in the nucleotides contained in the aptamer,
(i) the 2'-position of the ribose of each pyrimidine nucleotide is a fluorine atom,
(ii) the 2'-position of the ribose of each purine nucleotide is a hydroxy group;
(b) the aptamer of (a), wherein
(i) the fluorine atom at the 2'-position of the ribose of each pyrimidine nucleotide is independently unsubstituted, or substituted by an atom or group selected from the group consisting of a hydrogen atom, a hydroxy group and a methoxy group,
(ii) the hydroxy group at the 2'-position of the ribose of each purine nucleotide is independently unsubstituted, or substituted by an atom or group selected from the group consisting of a hydrogen atom, a methoxy group and a fluorine atom.

An aptamer refers to a nucleic acid molecule having a binding activity for a particular target molecule. The aptamer can inhibit the activity of a particular target molecule by binding to the particular target molecule. The aptamer of the present invention may be an RNA, a DNA, a modified nucleic acid or a mixture thereof. The aptamer of the present invention can also be in a linear or circular form.

The present invention provides an aptamer having a binding activity to FGF2. In one embodiment, the aptamer of the present invention can bind to FGF2 to inhibit the activity of FGF2. That is, the aptamer of the present invention may have an inhibitory activity on FGF2.

The inhibitory activity on FGF2 means an inhibitory capacity on any activity FGF2 has. For example, FGF2 acts on an FGF receptor-expressing cell to activate signal transduction and induce production of various cell growth factors and receptors thereof. Therefore, inhibitory activity on FGF2 can be an activity to inhibit intracellular signal transduction via an FGF receptor. Since expression of various such cell growth factors and receptors thereof results in the promotion of cell proliferation activity and cell migration activity, the inhibitory activity on FGF2 means inhibition of those activities.

Therefore, when the aptamer of the present invention binds to FGF2 and inhibits the binding of FGF2 and an FGF receptor, an action associated with the activation of intracellular signal transduction pathway via an FGF receptor, for example, suppression of cell death, cell proliferation, suppression of osteoprotegerin (OPG) production and the like can be inhibited.

FGF2 is a protein that is strongly expressed in the early development and differentiation, growth, regeneration and, for example, a protein having an amino acid sequence represented by Accession code EAX05222 or NP001997. FGF2 is sometimes also referred to as bFGF (basic FGF), FGFB or HBGF-2. In the present invention, FGF2 is produced in the body of an animal, or can also be produced from cultured cells such as mammalian cells of mouse and the like, insect cells, *Escherichia coli* and the like, or further can also be produced by chemical synthesis. When it is produced from cultured cells or by chemical synthesis, a variant can be easily produced by a method known per se. The "variant" of FGF2 means a protein or peptide having at least one activity from among the activities FGF2 inherently has, which has an amino acid sequence resulting from substitution, deletion, addition and the like of one to several amino acids of the known amino acid sequence of FGF2, or an amino acid sequence consisting of a part of the known amino acid sequence of FGF2. When an amino acid is substituted or added, said amino acid may be a natural amino acid or a non-natural amino acid. FGF2 in the present invention includes variants thereof.

The "FGF2 receptor" means a cell surface protein to which FGF2 binds. As the FGF2 receptor, FGFR1b, FGFR1c, FGFR2c, FGFR3c and FGFR4 are known. The FGF2 receptor referred to in the present invention may be a protein containing a natural amino acid sequence or a variant thereof. Here, the "variant" of the FGF2 receptor means a protein or peptide wherein one to several amino acids of an amino acid sequence have been substituted, deleted, added and the like, or having an amino acid sequence consisting of a part of the known amino acid sequence of FGF2 receptor, which has a binding activity to FGF2. In one embodiment, the present invention provides an aptamer that inhibits binding of FGF2 and an FGF2 receptor.

The aptamer of the present invention can exhibit inhibitory activity against FGF2 derived from any mammals. Such mammals include primates (e.g., human, monkey), rodents (e.g., mouse, rat and guinea pig), and companion animals, domestic animals and working animals (e.g., dog, cat, horse, bovine, goat, sheep, swine).

In one embodiment, the aptamer of the present invention can be characterized in that it can inhibit the activity of FGF2 but cannot inhibit the activity of FGF1. In addition, in one embodiment, the aptamer of the present invention can be characterized in that it can inhibit binding of FGF2 and an FGF2 receptor but cannot inhibit binding of FGF1 and an FGF1 receptor. FGF1 is an FGF family protein, and is most similar to FGF2.

In the above-mentioned formula (1), $N^1$ and $N^6$ are each independently any 0 to several bases, and $N^2$, $N^3$, $N^4$ and $N^5$ are independently any one base. In the present specification, "base" means any of adenine (A), guanine (G), cytosine (C), uracil (U) or thymine (T) constituting a nucleic acid.

While the base number of $N^1$ is not particularly limited as long as an aptamer containing a nucleotide sequence represented by the formula (1) binds to FGF2, it may be, for example, 0-about 10, 0-9, 0-8, 0-7, 0-6, 0-5, 0-4, 0-3, 0-2 and the like, preferably 0-2.

Similarly, while the base number of $N^6$ is not particularly limited, it may be, for example, 0-about 10, 0-9, 0-8, 0-7, 0-6, 0-5, 0-4, 0-3 and the like, preferably 0-10, 3-9, or 5-8.

In a preferable embodiment, in the above-mentioned formula (1),
$N^1$ is G, GG, AG, C or gap,
$N^2$ is A or U,
$N^3$ is G, C or A,
$N^4$ is G, C or U,
$N^5$ is G or U, and
$N^6$ is $UUCN^{61}$ or $AGUCN^{62}$ wherein $N^u$ and $N^{62}$ are each independently any 0 to several bases. Here, $N^1$ is a "gap" means that $N^1$ is absent in the formula (1), namely, $N^1$ is 0 base.

While the base number of $N^u$ is not particularly limited, it may be, for example, 0-about 10, 0-7, 0-6, 0-5, 0-4 and the like, preferably 0-5, 1-5, or 2-4.

While the base number of $N^{62}$ is also not particularly limited, it may be, for example, 0-about 10, 0-7, 0-5, 0-4, 0-3 and the like, preferably 0-5, 0-4, or 0-3.

In another preferable embodiment, in the above-mentioned formula (1),
$N^1$ is G, GG, AG or gap,
$N^2$ is A or U,
$N^3$ is G or A,
$N^4$ is C or U,
$N^5$ is G or U,
$N^6$ is $UUCN^{61}$ or $AGUCN^{62}$ wherein $N^u$ and $N^{62}$ are as defined above.

In a preferable embodiment, the aptamer of the present invention may contain a nucleotide sequence represented by the following formula (2) or (3):

GGGAAACUAGGGCGUUAACGUGACCAGU-
    GUUUC$N^{61}$           (formula 2) (SEQ ID NO:20)

$N^1$GGAUACUAGGGCAUUAAU-
    GUUACCAGUGUAGUC$N^{62}$    (formula 3) (SEQ ID NO:21)

wherein $N^1$, $N^{61}$ and $N^{62}$ are as defined above.

In a preferable embodiment, the aptamer of the present invention contains a nucleotide sequence shown by any of SEQ ID NOs: 1-12. The nucleotide sequences shown in SEQ ID NOs: 1-12 are given below (wherein uracil is optionally thymine) (hereinafter A, G, C and U show that the base of nucleotide is adenine, guanine, cytosine or uracil, respectively):

SEQ ID NO: 1:
    GGGAUACUAGGGCAUUAAUGUUACCAGUGUAGUCUCGA,

SEQ ID NO: 2:
    GGGAAACUAGGGCGUUAACGUGACCAGUGUUUCUCGA,

SEQ ID NO: 3:
    GGGAUACUAGGGCAUUAAUGUUACCAGUGUAGUCCC,

SEQ ID NO: 4:
    GGAUACUAGGGCAUUAAUGUUACCAGUGUAGUCC,

SEQ ID NO: 5:
    GGGGAUACUAGGGCAUUAAUGUUACCAGUGUAGUCCCC,

SEQ ID NO: 6:
    AGGGAUACUAGGGCAUUAAUGUUACCAGUGUAGUCCC,

SEQ ID NO: 7:
    GGGAAACUAGGGCGUUAACGUGACCAGUGUUUCCC,

SEQ ID NO: 8:
    CGGAUACUAGGGCAUUAAUGUUACCAGUGUAGUCCG,

SEQ ID NO: 9:
    CCGAUACUAGGGCAUUAAUGUUACCAGUGUAGUCGG,

SEQ ID NO: 10:
    GGGAUACUAGGGCGUUAACGUUACCAGUGUAGUCCC,

SEQ ID NO: 11:
    GGGAUACUAGGGCCUUAAGGUUACCAGUGUAGUCCC,

SEQ ID NO: 12:
    GGGAUACUAGGGCAUUUAUGUUACCAGUGUAGUCCC.

In one preferable embodiment, the aptamer of the present invention contains a nucleotide sequence shown in SEQ ID NO: 1, 3, 4, 5, 6, 8, 10 or 11.

In another preferable embodiment, the aptamer of the present invention contains a nucleotide sequence shown in SEQ ID NO: 2 or 7.

In still another preferable embodiment, the aptamer of the present invention contains a nucleotide sequence shown in SEQ ID NO: 1, 3, 4, 5 or 6.

In one embodiment, the aptamer of the present invention may contain, in any of the above-mentioned nucleotide sequences, a nucleotide sequence wherein 1 or several nucleotides are substituted, deleted, inserted or added, as long as the aptamer still binds to FGF2, and may be
(a) an aptamer wherein, in the nucleotides contained in the aptamer,
    (i) the 2'-position of the ribose of each pyrimidine nucleotide is a fluorine atom,
    (ii) the 2'-position of the ribose of each purine nucleotide is a hydroxy group,
(b) the aptamer of (a), wherein
    (i) the fluorine atom at the 2'-position of the ribose of each pyrimidine nucleotide is independently unsubstituted, or substituted by an atom or group selected from the group consisting of a hydrogen atom, a hydroxy group and a methoxy group,
    (ii) the hydroxy group at the 2'-position of the ribose of each purine nucleotide is independently unsubstituted, or substituted by an atom or group selected from the group consisting of a hydrogen atom, a methoxy group and a fluorine atom. As used herein, the number of the above-mentioned nucleotides substituted, deleted, inserted or added is not particularly limited as long as the aptamer still binds to FGF2 even after the substitution, deletion, insertion or addition. It can be, for example, 1-about 10, preferably 1-6, more preferably 1-5, further preferably 1-4, further preferably 1-3, most preferably 1 or 2. While the site of the nucleotide to be substituted, deleted, inserted or added is not particularly limited as long as the aptamer still binds to FGF2 even after the substitution, deletion, insertion or addition, at the sites specified to be one kind of nucleotide in the above-mentioned formula (1), (2) and (3), nucleotides are substituted, deleted, inserted or added at 1-3, preferably 1 or 2, more preferably 1, site. On the other hand, when plural kinds of nucleotides may be present in the formulas (1), (2) and (3), more number of nucleotides (e.g., 1-about 10, preferably 1-6, more preferably 1-5, further preferably 1-4) may be substituted, deleted, inserted or added.

The length of the aptamer of the present invention is not particularly limited, and can usually be about 10 to about 200 nucleotides and can be, for example, not less than about 20 nucleotides (e.g., not less than 25 nucleotides, not less than 30 nucleotides, not less than 31 nucleotides, not less than 32 nucleotides, not less than 33 nucleotides), preferably not less than 25 nucleotides, more preferably not less than 30 nucleotides, further preferably not less than 33 nucleotides. In addition, it can be, for example, not more than about 100 nucleotides, generally not more than about 80 nucleotides, preferably not more than about 70 nucleotides, more preferably not more than about 60 nucleotides, further preferably not more than about 50 nucleotides, further preferably not more than about 45 nucleotides (e.g., not more than 44 nucleotides, not more than 43 nucleotides, not more than 42 nucleotides, not more than 41 nucleotides, not more than 40 nucleotides). When the total number of nucleotides is smaller, chemical synthesis and mass-production will be easier, and there is a major advantage in terms of cost. It is also thought that chemical modification is easy, stability in the body is high, and toxicity is low.

Therefore, the length of the aptamer of the present invention may be generally about 10-about 200 nucleotides, preferably 20-80 nucleotides, more preferably 25-60 nucleotides, further preferably 25-50 nucleotides, most preferably 30-45 nucleotides.

The aptamer of the present invention may be a conjugate selected from the group consisting of a conjugate of plural aptamers containing a nucleotide sequence represented by the m above-mentioned formula (1) (aptamer (A)), a conjugate of plural aptamers containing a nucleotide sequence wherein 1 or several nucleotides are substituted, deleted, inserted or added in the nucleotide sequence represented by the above-mentioned formula (1) (aptamer (B)), and a conjugate of 1 or plural aptamers (A) and 1 or plural aptamers (B). These conjugates can also bind to FGF2.

Here, conjugation can be achieved by tandem binding. In the conjugation, a linker may be utilized. As the linker, nucleotide chains (e.g., 1 to about 20 nucleotides) and non-nucleotide chains (e.g., —(CH$_2$)$_n$— linker, —(CH$_2$CH$_2$O)$_n$— linker, hexaethylene glycol linker, TEG linker, peptide-containing linker, —S—S— bond-containing linker, —CONH— bond-containing linker, —OPO$_3$— bond-containing linker) can be mentioned. The plurality as mentioned in the above-described conjugate of a plurality thereof is not particularly limited, as long as it is two or more, and the plurality can be, for example, 2, 3 or 4.

Each nucleotide contained in the aptamer of the present invention is the same or different and can be a nucleotide comprising a hydroxyl group at the 2' position of ribose (e.g., ribose of pyrimidine nucleotide, ribose of purine nucleotide) (i.e., a natural nucleotide) or a nucleotide wherein hydroxyl group is substituted (modified) by any atom or group at the 2' position of ribose (sometimes to be indicated as "modified nucleotide" in the present invention).

As examples of any such atom or group, a nucleotide substituted by a hydrogen atom, a fluorine atom or an —O-alkyl group (e.g., —O-Me group), an —O-acyl group (e.g., —O—CHO group), or an amino group (e.g., —NH$_2$ group) can be mentioned.

In the aptamer of the present invention, at least one kind (e.g., 1, 2, 3 or 4 kinds) of nucleotide can also be a modified nucleotide comprising a hydroxyl group, or the above-described any atom or group, for example, at least two kinds (e.g., 2, 3 or 4 kinds) of groups selected from the group consisting of a hydrogen atom, a fluorine atom, a hydroxyl group and a —O-Me group, at the 2' position of ribose.

In the aptamer of the present invention, all pyrimidine nucleotides may be nucleotides wherein the 2'-position of ribose is a fluorine atom, or may be the same or different and nucleotides wherein fluorine atom is unsubstituted, or substituted by any atom or group mentioned above, preferably an atom or group selected from the group consisting of a hydrogen atom, a hydroxyl group and a methoxy group. Particularly, when a production method using the below-mentioned DuraScribe™ T7 Transcription Kit (manufactured by Epicentre) is applied as a production method of the aptamer of the present invention, an aptamer wherein the 2'-position of ribose of all pyrimidine nucleotides is fluorinated can be obtained. The aptamer of the present invention wherein fluorine atom is substituted by other above-mentioned atom or group can be produced by the below-mentioned method.

In the aptamer of the present invention, all purine nucleotides may be nucleotides wherein the 2'-position of ribose is a fluorine atom, or may be the same or different and nucleotides wherein hydroxy group is unsubstituted, or a nucleotide substituted by any atom or group mentioned above, preferably an atom or group selected from the group consisting of a hydrogen atom, a hydroxyl group and a methoxy group at the 2' position of ribose. The aptamer of the present invention wherein a hydroxyl group is substituted by other above-mentioned atom or group can be produced by the below-mentioned method.

In the aptamer of the present invention, all pyrimidine nucleotides may be nucleotides wherein the fluorine atom at the 2'-position of ribose is substituted by any of the aforementioned atoms or groups, for example, the same atoms or groups selected from the group consisting of a hydrogen atom, a hydroxy group and an —O-Me group.

In the aptamer of the present invention, moreover, all purine nucleotides may be nucleotides wherein the hydroxy group at the 2'-position of ribose is substituted by any of the aforementioned atoms or groups, for example, the same atoms or groups selected from the group consisting of a hydrogen atom, a fluorine atom and an —O-Me group.

In a preferable embodiment, each pyrimidine nucleotide contained in the aptamer of the present invention is a nucleotide containing a fluorine atom at the 2'-position of ribose, and each purine nucleotide is a nucleotide having a hydroxy group at the 2'-position of ribose. In another embodiment, the above-mentioned fluorine atom at the 2'-position of the ribose of each pyrimidine nucleotide is independently optionally substituted by an atom or group selected from the group consisting of a hydrogen atom, a hydroxy group and a methoxy group, and the above-mentioned hydroxy group at the 2'-position of the ribose of each purine nucleotide is optionally independently substituted by an atom or group selected from the group consisting of a hydrogen atom, a methoxy group and a fluorine atom.

In this Description, the nucleotides constituting the aptamer are assumed to be RNAs (i.e., the sugar groups are assumed to be ribose) in describing how the sugar groups are modified in the nucleotides. However, this does not mean that DNA is exempted from the aptamer-constituting nucleotides, and a modification of RNA should read as a modification of DNA as appropriate. When the nucleotide constituting the aptamer is DNA, for example, replacement of the hydroxyl group at the 2'-position of ribose by X should read as a replacement of a hydrogen atom at the 2'-position of deoxyribose by X.

When uracil is substituted with thymine in the aptamer of the present invention, FGF2-binding activity, FGF2-FGF receptor binding inhibitory activity, stability, drug deliverability and stability in blood of the aptamer and the like can be increased.

In the aptamer of the present invention, 1 or several, for example, 1-2, 1-3, 1-4, 1-5 nucleotides of phosphoric acid diester bond in the nucleotide may be modified or substituted by any substituent(s). For example, phosphoric acid diester bond may be substituted by a phosphorothioate bond, a phosphorodithioate bond, an alkylphosphonate bond, a phosphoramidate bond and the like. Here, for example, "nucleotide is substituted by a phosphorothioate bond" means that a phosphoric acid group at a binding site between adjacent nucleotides is sulfurated, that is, a phosphodiester bond is altered to a phosphorothioate bond.

In the aptamer of the present invention, one or several, for example, 1-2, 1-3, 1-4, 1-5 nucleotides may be substituted by Bridged Nucleic Acid (BNA) or Locked Nucleic Acid (LNA) to stabilize aptamer and improve the activity thereof. As used herein, the "bridged nucleic acid" refers to one having a structure wherein the binding affinity to a complementary sequence is enhanced by restricting the degree of freedom of nucleic acid by intramolecular crosslinking, and acquire nuclease resistance. Examples thereof include, but are not limited to, 2',4'-BNA (Locked Nucleic Acid (LNA)), 2'-O,4'-C-ethylene-bridged Nucleic Acid (ENA) and the like.

The aptamer of the present invention is an aptamer that binds to FGF2, further preferably an aptamer that can bind to FGF2 to inhibit binding of FGF2 and an FGF receptor. Whether the aptamer of the present invention inhibits the binding of FGF2 and an FGF receptor can be evaluated by a test utilizing, for example, the surface plasmon resonance method of Example 1 m and the like.

The aptamer of the present invention may be one wherein a sugar residue (e.g., ribose) of each nucleotide has been modified to increase the FGF2 binding activity, stability, drug deliverability and the like. As examples of the modification in a sugar residue, replacement of oxygen atom at the 2'-position, 3'-position and/or 4'-position of the sugar residue with another atom, and the like can be mentioned. As the kind of the modification, fluorination, O-alkylation (e.g., O-methylation, O-ethylation), O-arylation, S-alkylation (e.g., S-methylation, S-ethylation), S-arylation, and amination (e.g., —$NH_2$) can be mentioned. In addition, examples thereof include 4'-SRNA wherein the 4'-position oxygen is replaced with sulfur, LNA (Locked Nucleic Acid) wherein the 2'-position and the 4'-position are crosslinked via methylene, 3'-N-phosphoramidate nucleic acid wherein the 3'-position hydroxyl group is replaced with an amino group and the like. The aptamer of the present invention is sometimes produced with a given modification of the oxygen atom at the 2'-position of ribose of pyrimidine nucleotide, due to the production method thereof. When a production method using the below-mentioned DuraScribe™ T7 Transcription Kit (manufactured by Epicentre) is applied as a production method of the aptamer of the present invention, an aptamer wherein the 2'-position of ribose of preferably all pyrimidine nucleotides is fluorinated is produced. Therefore, it is possible to produce various variations of aptamers having enhanced activity even though the base sequence is the same, by applying such alteration in the sugar residue to the obtained aptamer. From the above, the aptamer of the present invention can be preferably an aptamer wherein a sugar residue of at least one nucleotide is modified. Such alterations in the sugar residue can be performed by a method known per se (see, for example, Sproat et al., (1991) Nucl. Acid. Res. 19, 733-738; Cotton et al., (1991) Nucl. Acid. Res. 19, 2629-2635; Hobbs et al., (1973) Biochemistry 12, 5138-5145). To be specific, an aptamer wherein the hydroxyl group at the 2'-position of ribose is substituted by an atom or group selected from the group consisting of a hydrogen atom, a hydroxyl group and a methoxy group can be produced by using, as a base, an aptamer wherein the hydroxyl group at the 2'-position of ribose of all pyrimidine nucleotides is substituted by a fluoro group.

The aptamer of the present invention may also have a nucleic acid base (e.g., purine or pyrimidine) altered (e.g., chemical substitution) to increase the FGF2 binding activity, stability, drug deliverability and the like. As examples of such alterations, pyrimidine alteration at 5-position, purine alteration at 6- and/or 8-position(s), alteration with an extracyclic amine, substitution with 4-thiouridine, and substitution with 5-bromo or 5-iodo-uracil can be mentioned. The phosphate group contained in the aptamer of the present invention may be altered to confer resistance to nuclease and hydrolysis. For example, the P(O)O group may be replaced with P(O)S (thioate), P(S)S (dithioate), P(O)N(R)R' (amidate), P(O)R, P(O)OR, CO or $CH_2$ (formacetal) or 3'-amine (—NH—$CH_2$—$CH_2$—) [wherein each unit of R or R' is independently H or a substituted or unsubstituted alkyl (e.g., methyl, ethyl)].

The linking group is, for example, —O—, —N— or —S—, and nucleotides can bind to an adjoining nucleotide via these linking groups.

The alterations may also include alterations such as capping at 3' and 5'.

An alteration can further be performed by adding to an end a polyethyleneglycol, amino acid, peptide, inverted dT, nucleic acid, nucleosides, Myristoyl, Lithocolic-oleyl, Docosanyl, Lauroyl, Stearoyl, Palmitoyl, Oleoyl, Linoleoyl, other lipids, steroids, cholesterol, caffeine, vitamins, dyes, fluorescent substances, anticancer agents, toxins, enzymes, radioactive substances, biotin and the like. For such alterations, see, for example, U.S. Pat. Nos. 5,660,985 and 5,756,703.

Particularly, when alteration is performed by terminus addition of PEG, the molecular weight of PEG is not particularly limited, and is preferably 1000-100000, more preferably 30000-90000. PEG may be linear or branched into two or more chains (multi-arm PEG).

Such PEG is not particularly limited, and those of ordinary skill in the art can appropriately select and use commercially available or known PEG (e.g., www.peg-drug.com/peg_product/branched.html). Specific preferable examples of the PEG to be applied to the aptamer of the present invention include 2-branched GS type PEG having a molecular weight of 40000 (SUNBRIGHT GL2-400GS manufactured by NOF CORPORATION), 2-branched TS type PEG having a molecular weight of 40000 (SUNBRIGHT GL2-400TS manufactured by NOF CORPORATION), 4-branched TS type PEG having a molecular weight of 40000 (SUNBRIGHT GL4-400TS manufactured by NOF CORPORATION), 2-branched TS type PEG having a molecular weight of 80000 (SUNBRIGHT GL2-800TS manufactured by NOF CORPORATION), 4-branched TS type PEG having a molecular weight of 80000 (SUNBRIGHT GL4-800TS manufactured by NOF CORPORATION) and the like.

In this case, in the aptamer of the present invention, PEG may be directly added to the terminus. It is more preferable that a linker having a group bindable to PEG and the like be added to the terminus thereof, and PEG be added to the aptamer of the present invention via the linker.

The linker for PEG and the aptamer of the present invention is not particularly limited, and carbon chain number, functional group and the like can be appropriately selected according to the binding site, the kind of PEG and the like. Examples of such linker include a linker having an amino group. Specifically, when added to the 5' end, ssH Linker (SAFC) or DMS(O)MT-AMINO-MODIFIER (GLEN RESEARCH) can be mentioned, and when added to the 3' end, TFA Amino C-6 lcaa CPG (ChemGenes) and the like can be mentioned. When this linker is selected, for example, an active group of N-hydroxysuccinimide is added to PEG, and reacted with an amino group on the linker side, whereby the aptamer of the present invention can be bound to PEG via the linker.

As PEG and linker, commercially available products can be preferably used. The reaction conditions and the like relating to the binding of PEG, a linker and the aptamer of the present invention can be appropriately determined by those of ordinary skill in the art.

The aptamer of the present invention can be chemically synthesized as disclosed herein and by a method known per se in the art. An aptamer binds to the target substance in a wide variety of binding modes, such as ionic bonds based on the negative charge of the phosphate group, hydrophobic bonds and hydrogen bonds based on ribose, and hydrogen bonds and stacking interaction based on nucleic acid bases. In particular, ionic bonds based on the negative charge of the phosphate group, which are present in the same number as the number of constituent nucleotides, are strong, and bind to lysine and arginine being present on the surface of the positive charge of protein. For this reason, nucleic acid bases not involved in the direct binding to the target substance can be substituted. In particular, because the region of stem structure has already formed base pairs and faces the inside of the double helical structure, nucleic acid bases are unlikely to bind directly to the target substance. Therefore, even when a base pair is substituted with another base pair, the activity of the aptamer often does not decrease. In structures wherein no base pairs are formed, such as loop structures, provided that the nucleic acid base is not involved in the direct binding to the target molecule, base substitution is possible. Regarding modifications of the 2'-position of ribose, the functional group at the 2'-position of ribose infrequently interacts directly with the target molecule, but in many cases, it is of no relevance, and can be substituted by another modified molecule. Hence, an aptamer, unless the functional group involved in the direct binding to the target molecule is substituted or deleted, often retains the activity thereof. It is also important that the overall three-dimensional structure does not change substantially.

An aptamer can be prepared by utilizing the SELEX method or an improved version thereof (e.g., Ellington et al., (1990) Nature, 346, 818-822; Tuerk et al., (1990) Science, 249, 505-510). In the SELEX method, by increasing the number of rounds or using a competing substance, an aptamer exhibiting a stronger binding potential for the target substance is concentrated and selected. Hence, by adjusting the number of rounds of SELEX and/or changing the competitive condition, aptamers with different binding forces, aptamers with different binding modes, and aptamers with the same binding force or binding mode but different base sequences can be obtained in some cases. The SELEX method comprises a process of amplification by PCR; by causing a mutation by using manganese ions and the like in the process, it is possible to perform SELEX with higher diversity.

The aptamers obtained by SELEX are nucleic acids that exhibit high affinity for the target substance, but this does not mean binding to an active site of the target substance. Therefore, the aptamers obtained by SELEX do not necessarily act on the function of the target substance. FGF2 is a basic protein, and is thought to be likely to allow nucleic acids to bind thereto nonspecifically. An aptamer that does not bind to an active site does not influence the activity of the target substance. In fact, the RNA used for control did not inhibit the binding of FGF2 and an FGF2 receptor.

Using the active aptamer thus selected, optimized SELEX can be performed to obtain an aptamer possessing higher activity. In the optimized SELEX, SELEX is performed again after preparing a template wherein an aptamer with a determined sequence is partially randomized or a template doped with about 10 to 30% of random sequences.

An aptamer obtained by SELEX has a length of about 80 nucleotides, and this is difficult to prepare as a pharmaceutical as it is. Hence, it is preferably to repeat try-and-error efforts to shorten the aptamer to a length permitting easy chemical synthesis (e.g., about 60 nucleotides or less, more preferably about 50 nucleotides or less, most preferably 45 nucleotides or less, enabling chemical synthesis).

Depending on the primer design for an aptamer obtained by SELEX, the ease of the subsequent minimization operation changes. Unless the primer is designed successfully, subsequent development will be impossible even if an aptamer with activity is selected by SELEX.

Aptamers are altered easily since they permit chemical synthesis. For aptamers, by predicting the secondary structure using the MFOLD program, or by predicting the steric structure by X-ray analysis or NMR analysis, it is possible to predict to some extent which nucleotide can be substituted or deleted, and where to insert a new nucleotide. A predicted aptamer with the new sequence can easily be chemically synthesized, and it can be determined whether or not the aptamer retains the activity using an existing assay system.

When a region important to the binding of the obtained aptamer with the target substance is identified by repeated try-and-error efforts as described above, the activity remains unchanged in many cases even when a new sequence is added to both ends of the sequence. The length of the new sequence is not particularly limited.

As mentioned earlier, modifications, like sequences, permit a wide range of design or alterations.

As stated above, aptamers permit a wide range of design or alterations. The present invention also provides a production method of aptamer that enables a wide range of design or alteration of an aptamer comprising a specified sequence (e.g., a sequence corresponding to a portion selected from among stem regions, internal loop regions, hairpin loop regions and single-strand regions: hereinafter, abbreviated as fixed sequence as required).

For example, the production method of such aptamer includes production of an aptamer comprising a fixed sequence by using a single kind of nucleic acid molecule consisting of a nucleotide sequence shown by:

Primer sequence (i)-(N)a-fixed sequence-(N)b-Primer sequence (ii)

wherein (N)a represents a nucleotide chain consisting of "a" units of N; (N)b represents a nucleotide chain consisting of "b" units of N; each of the units of N, whether identical or different, is a nucleotide selected from the group consisting of A, G, C, U and T (preferably, A, G, C and U). Each of "a" and "b", whether identical or different, can be any numbers, and can be, for example, 1 to about 100, preferably 1 to about 50, more preferably 1 to about 30, still more preferably 1 to about 20 or 1 to about 10], or plural kinds of nucleic acid molecules (e.g., library of nucleic acid molecule different in the number of a, b etc.) and primer pairs corresponding to the primer sequences (i) and (ii), respectively.

Preferred as the aptamer of the present invention is an aptamer of any of the following (a'), (b') or (c'), which binds to FGF2 and inhibits binding of FGF2 and an FGF receptor:

(a') an aptamer containing a nucleotide sequence shown in any of SEQ ID NOs: 1-7 (or SEQ ID NO: 2 or 7, or any of SEQ ID NOs: 1 and 3-6) (wherein uracil may be thymine), wherein, in the nucleotides contained in the aptamer, (i) the 2'-position of the ribose of each pyrimidine nucleotide is a fluorine atom, (ii) the 2'-position of the ribose of each purine nucleotide is a hydroxy group;

(b') an aptamer containing a nucleotide sequence wherein 1-5 (or 1-4 or 1-3) nucleotides are substituted, deleted, inserted or added in the nucleotide sequence shown in any of SEQ ID NO: 1-7 (or SEQ ID NO: 2 or 7, or any of SEQ ID NOs: 1 and 3-6) (wherein uracil may be thymine), wherein, in the nucleotide contained in the aptamer, (i) the 2'-position of ribose of each pyrimidine nucleotide is a fluorine atom, (ii) the 2'-position of ribose of each purine nucleotide is a hydroxy group; or (c') the aptamer wherein, in the aptamer of (a') or (b'), (i) the fluorine atom at the 2'-position of the ribose of each pyrimidine nucleotide is independently unsubstituted, or substituted by an atom or group selected from the group consisting of a hydrogen atom, a hydroxy group and a methoxy group, (ii) the hydroxy group at the 2'-position of the ribose of each purine nucleotide is independently unsubstituted or substituted by an atom or group selected from the group consisting of a hydrogen atom, a methoxy group and a fluorine atom, and further preferred is, of the above-mentioned aptamers, an aptamer having a nucleotide length of 30-45 nucleotides.

The present invention also provides a complex comprising the aptamer of the present invention and a functional substance bound thereto. The binding between the aptamer and the functional substance in the complex of the present invention can be a covalent bond or a non-covalent bond. The complex of the present invention can be one wherein the aptamer of the present invention and one or more (e.g., 2 or 3) of functional substances of the same kind or different kinds are bound together. The functional substance is not particularly limited, as far as it newly confers a certain function to an aptamer of the present invention, or is capable of changing (e.g., improving) a certain characteristic which an aptamer of the present invention can possess. As examples of the functional substance, proteins, peptides, amino acids, lipids, sugars, monosaccharides, polynucleotides, and nucleotides can be mentioned. As examples of the functional substance, affinity substances (e.g., biotin, streptavidin, polynucleotides possessing affinity for target complementary sequence, antibodies, glutathione Sepharose, histidine), substances for labeling (e.g., fluorescent substances, luminescent substances, radioisotopes), enzymes (e.g., horseradish peroxidase, alkaline phosphatase), drug delivery vehicles (e.g., liposome, microspheres, peptides, polyethyleneglycols), drugs (e.g., those used in missile therapy such as calicheamycin and duocarmycin; nitrogen mustard analogues such as cyclophosphamide, melphalan, ifosfamide or trofosfamide; ethylenimines such as thiotepa; nitrosoureas such as carmustine; alkylating agents such as temozolomide or dacarbazine; folate-like metabolic antagonists such as methotrexate or raltitrexed; purine analogues such as thioguanine, cladribine or fludarabine; pyrimidine analogues such as fluorouracil, tegafur or gemcitabine; *vinca* alkaloids such as vinblastine, vincristine or vinorelbine and analogues thereof; podophyllotoxin derivatives such as etoposide, taxans, docetaxel or paclitaxel; anthracyclines such as doxorubicin, epirubicin, idarubicin and mitoxantrone, and analogues thereof; other cytotoxic antibiotics such as bleomycin and mitomycin; platinum compounds such as cisplatin, carboplatin and oxaliplatin; pentostatin, miltefosine, estramustine, topotecan, irinotecan and bicalutamide), and toxins (e.g., ricin toxin, liatoxin and Vero toxin) can be mentioned. These functional molecules are finally removed in some cases. Furthermore, the molecules may be peptides that can be recognized and cleaved by enzymes such as thrombin, matrix metalloproteinase (MMP), and Factor X, and may be polynucleotides that can be cleaved by nucleases or restriction endonuclease.

The aptamer or the complex of the present invention can be used as, for example, a medicament, a diagnostic reagent, a test reagent or a reagent. Particularly, it is useful as a medicament for the treatment or prophylaxis of diseases accompanied by angiogenesis such as age-related macular degeneration and the like, bone-articular diseases such as osteoporosis, rheumatoid arthritis, osteoarthritis, bone fracture and the like, or pain, or a diagnostic agent, a test reagent or a reagent.

The medicament of the present invention can be one formulated with a pharmaceutically acceptable carrier. As examples of the pharmaceutically acceptable carrier, excipients such as sucrose, starch, mannit, sorbit, lactose, glucose, cellulose, talc, calcium phosphate, and calcium carbonate; binders such as cellulose, methylcellulose, hydroxylpropylcellulose, polypropylpyrrolidone, gelatin, gum arabic, polyethylene glycol, sucrose, and starch; disintegrants such as starch, carboxymethylcellulose, hydroxylpropylstarch, sodium-glycol-starch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizinammonium salt, glycine, and orange powder; preservatives such as sodium benzoate, sodium hydrogen sulfite, methylparaben, and propylparaben; stabilizers such as citric acid, sodium citrate, and acetic acid; suspending agents such as methylcellulose, polyvinylpyrrolidone, and aluminum stearate; dispersing agents such as surfactants; diluents such as water, physiological saline, and orange juice; base waxes such as cacao butter, polyethylene glycol, and kerosene; and the like can be mentioned, but these are not limitative.

Preparations suitable for oral administration are a solution prepared by dissolving an effective amount of ligand in a diluent such as water, physiological saline, or orange juice; capsules, sachets or tablets comprising an effective amount of ligand in solid or granular form; a suspension prepared by suspending an effective amount of active ingredient in an appropriate dispersant; an emulsion prepared by dispersing and emulsifying a solution of an effective amount of active ingredient in an appropriate dispersant, and the like.

The medicament of the present invention can be coated by a method known per se for the purpose of taste masking, enteric dissolution, sustained release and the like as necessary. As examples of coating agents used for the coating, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (manufactured by Rohm, Germany, methacrylic acid/acrylic acid copolymer), dyes (e.g., red iron oxide, titanium dioxide and the like) and the like are used. The medicament may be a rapid-release preparation or sustained-release preparation. Examples of the base of the sustained-release preparation include liposome, atelocollagen, gelatin, hydroxyapatite, PLGA and the like.

As preparations suitable for parenteral administration (e.g., intravenous administration, subcutaneous administration, intramuscular administration, topical administration, intraperitoneal administration, intranasal administration, pulmonary administration and the like), aqueous and non-aqueous isotonic sterile injectable liquids are available, which may comprise an antioxidant, a buffer solution, a bacteriostatic agent, an isotonizing agent and the like. Aqueous and non-aqueous sterile suspensions can also be mentioned, which may comprise a suspending agent, a solubilizer, a thickener, a stabilizer, an antiseptic and the like. The preparation can be included in a container such as an ampoule or a vial in a unit dosage volume or in several divided doses. An active ingredient and a pharmaceutically acceptable carrier can also be freeze-dried and stored in a state that may be dissolved or suspended in an appropriate sterile vehicle just before use. In addition to liquid injections, inhalants and ointments are also acceptable. In the case of an inhalant, an active ingredient in a freeze-dried state is micronized and administered by inhalation using an appropriate inhalation device. An inhalant can be formulated as appropriate with a conventionally used surfactant, oil, seasoning, cyclodextrin or derivative thereof and the like as required.

Here, as examples of the surfactant, oleic acid, lecithin, diethylene glycol dioleate, tetrahydroflufuryl oleate, ethyl oleate, isopropyl myristate, glyceryl trioleate, glyceryl monolaurate, glyceryl monooleate, glyceryl monostearate, glyceryl monolysinoate, cetyl alcohol, stearyl alcohol, polyethyleneglycol 400, cetylpyridinium chloride, sorbitan trioleate (trade name, Span 85), sorbitan monoleate (trade name, Span 80), sorbitan monolaurate (trade name, Span 20), polyoxyethylene hardened castor oil (trade name, HCO-60), polyoxyethylene (20) sorbitan monolaurate (trade name, Tween 20), polyoxyethylene (20) sorbitan monooleate (trade name, Tween 80), lecithin of natural resource origin (trade name, Epiclon), oleylpolyoxyethylene (2) ether (trade name, Brij 92), stearyl polyoxyethylene (2) ether (trade name, Brij 72), lauryl polyoxyethylene (4) ether (trade name, Brij 30), oleylpolyoxyethylene (2) ether (trade name, Genapol 0-020), block copolymer of oxyethylene and oxypropylene (trade name, Synperonic) and the like can be mentioned. Span, Tween, Epiclon, Brij, Genapol and Synperonic are trademarks.

As examples of the oil, corn oil, olive oil, cottonseed oil, sunflower oil and the like can be mentioned. In the case of an ointment, an appropriate pharmaceutically acceptable base (yellow petrolatum, white petrolatum, paraffin, plastibase, silicone, white ointment, beeswax, lard, vegetable oils, hydrophilic ointment, hydrophilic petrolatum, purified lanolin, hydrolyzed lanolin, water-absorbing ointment, hydrophilic plastibase, macrogol ointment and the like) is blended with an active ingredient, and used as a preparation.

An inhalant can be produced according to a conventional method. Specifically, an inhalant can be produced by powdering or liquefying the above-described aptamer and complex of the present invention, blending it in an inhalation propellant and/or carrier, and filling them in an appropriate inhalation vessel. When the above-described aptamer and complex of the present invention is a powder, an ordinary mechanical powder inhalator can be used; in the case of a liquid, an inhalator such as a nebulizer can be used. Here, as the propellant, conventionally known one can be widely used; chlorofluorocarbon-series compounds such as chlorofluorocarbon-11, chlorofluorocarbon-12, chlorofluorocarbon-21, chlorofluorocarbon-22, chlorofluorocarbon-113, chlorofluorocarbon-114, chlorofluorocarbon-123, chlorofluorocarbon-142c, chlorofluorocarbon-134a, chlorofluorocarbon-227, chlorofluorocarbon-0318, and 1,1,1,2-tetrafluoroethane, hydrocarbons such as propane, isobutane, and n-butane, ethers such as diethyl ether, compressed gases such as nitrogen gas and carbon dioxide gas and the like can be mentioned.

When the medicament of the present invention is used as a medicament for the prophylaxis or treatment of the above-mentioned diseases, the medicament of the present invention can be directly administered to a lesion, or administered according to the above-mentioned other methods.

Since the aptamer of the present invention is a single strand nucleic acid, detoxification by the administration of a nucleotide containing a complementary sequence is possible, and has a high possibility of making a pharmaceutical product with higher safety than a neutralizing antibody which is difficult to control dynamically after administration. This is an extremely advantageous aspect in view of the problem of infections possibly occurring in the antibody in the drug treatment and the like, which is caused by a long retention time of antibody in the body. Particularly, when the medicament of the present invention is used as a medicament for the prophylaxis or treatment of the above-mentioned diseases, it is obvious, in consideration of the severity of disease and the risk of side effects, that a medicament having higher safety can be obtained by utilizing an aptamer permitting easy control of in vivo kinetics.

The dosage of the medicament of the present invention varies depending on the kind and activity of active ingredient, seriousness of disease, animal species being the subject of administration, drug tolerability of the subject of administration, body weight, age and the like, and the usual dosage, based on the amount of active ingredient per day for an adult, can be about 0.0001 to about 100 mg/kg, for example, about 0.0001 to about 10 mg/kg, preferably about 0.005 to about 1 mg/kg.

In addition, the aptamer or complex of the present invention can also be used as a drug delivery agent, probe for in vivo imaging, probe for measuring blood concentration of FGF2, probe for tissue staining, probe for ELISA, ligand for FGF2 separation and purification.

The present invention also provides a solid phase carrier having the aptamer and the complex of the present invention immobilized thereon. As examples of the solid phase carrier, a substrate, a resin, a plate (e.g., multiwell plate), a filter, a cartridge, a column, and a porous material can be mentioned. The substrate can be one used in DNA chips, protein chips and the like; for example, nickel-PTFE (polytetrafluoroethylene) substrates, glass substrates, apatite substrates, silicone substrates, alumina substrates and the like, and substrates prepared by coating these substrates with a polymer and the like can be mentioned. As examples of the resin, agarose particles, silica particles, a copolymer of acrylamide and N,N'-methylenebisacrylamide, polystyrene-crosslinked divinylbenzene particles, particles of dextran crosslinked with epichlorohydrin, cellulose fiber, crosslinked polymers of aryldextran and N,N'-methylenebisacrylamide, monodispersed synthetic polymers, monodispersed hydrophilic polymers, Sepharose, Toyopearl and the like can be mentioned, and also resins prepared by binding various functional groups to these resins were included. The solid phase carrier of the present invention can be useful in, for example, purifying, detecting and quantifying FGF2.

The aptamer and the complex of the present invention can be immobilized onto a solid phase carrier by a method known per se. For example, a method that introduces an affinity substance (e.g., those described above) or a predetermined functional group into the aptamer or the complex of the present invention, and then immobilizes the aptamer and complex onto a solid phase carrier via the affinity substance or predetermined functional group can be mentioned. The present invention also provides a method of immobilizing the aptamer or complex of the present invention on a solid phase carrier, and a solid phase carrier obtained thereby. The predetermined functional group can be a functional group that can be subjected to a coupling reaction; for example, an amino group, a thiol group, a hydroxyl group, and a carboxyl group can be mentioned. The present invention also provides an aptamer having such a functional group introduced thereto.

The present invention also provides a method of purifying and concentrating FGF2. In particular, the purification method of the present invention makes it possible to separate FGF2 from other FGF family proteins. The method of purification and concentration of the present invention can comprise adsorbing FGF2 to the solid phase carrier of the present invention, and eluting the adsorbed FGF2 with an eluent. Adsorption of FGF2 to the solid phase carrier of the present invention can be achieved by a method known per se. For example, a FGF2-containing sample (e.g., bacterial or cell culture or culture supernatant, blood) is introduced into the solid phase carrier of the present invention or a composition containing the same. FGF2 can be eluted using an eluent such as a neutral solution. There is no limitation on the neutral eluent, which can have a pH of, for example, about 6 to about 9, preferably about 6.5 to about 8.5, and more preferably about 7 to about 8. The neutral solution can also comprise, for example, a potassium salt (e.g., KCl), a magnesium salt (e.g., $MgCl_2$), a surfactant (e.g., Tween 20, Triton, NP40), and glycerin.

The method of purification and concentration of the present invention can further comprise washing the solid phase carrier using a washing solution after FGF2 adsorption. Examples of the washing solution include those containing urea, a chelating agent (e.g., EDTA), Tris, an acid, an alkali, Transfer RNA, DNA, surfactants such as Tween 20, salts such as NaCl and the like. The method of purification and concentration of the present invention can still further comprise heating the solid phase carrier. This step enables the regeneration and sterilization of the solid phase carrier.

The aptamer or complex of the present invention can be utilized as a detection probe, particularly, detection probe of FGF2. A labeling method of aptamer is not particularly limited, and a method known per se is applicable. Examples of such method include labeling with radioisotope, labeling with fluorescence dye or fluorescence protein, and the like.

The present invention also provides a method of detecting and quantifying FGF2. In particular, the present invention makes it possible to detect and quantify FGF2 separately from the proteins of other family proteins. The method of detection and quantitation of the present invention can comprise measuring FGF2 by utilizing the aptamer of the present invention (e.g., by the use of the complex and solid phase carrier of the present invention). The method of detecting and quantifying FGF2 can be performed in the same manner as an immunological method, except that the aptamer of the present invention is used in place of an antibody. Therefore, by using the aptamer of the present invention in place of an antibody, m in the same manner as such methods as enzymeimmunoassay (EIA) (e.g., direct competitive ELISA, indirect competitive ELISA, sandwich ELISA), radioimmunoassay (RIA), fluorescent immunoassay (FIA), Western blot method, immunohistochemical staining method, and cell sorting method, detection and quantitation can be performed. These methods can be useful in, for example, measuring FGF2 contents in living organisms or biological samples, and in diagnosing a disease associated with FGF2.

The disclosures in all publications mentioned herein, including patents and patent application specifications, are incorporated by reference herein in the present invention to the extent that all of them have been given expressly.

Examples of particular embodiments for the practice of the present invention are shown below. Examples are provided for explanation purposes only, and are not at all intended to limit the scope of the present invention.

EXAMPLES

Example 1: Preparation of RNA Aptamers that Bind Specifically to FGF2

In a conventional SELEX method, a library of about 30 mer-40 mer random sequence added with about 20 mer primers on the both termini was use. In this case, the full-length of the obtained aptamer is about 80-100 mer, and a chain shortening was necessary thereafter. However, chain shortening is not necessarily simple and easy, and the activity frequently decreased radically. Thus, by reference to the Tailored-SELEX method developed by NOXXON (Vater et al. Nucleic Acids Res. 31, 2003, e130; Jarosch et al. Nucleic Acids Res. 34, 2006, e86), SELEX using an RNA pool with a length of about 30 mer which excludes primer sequence was performed.

The DNA template and primer sequences used are as described below.

```
DNA template:
                                          (SEQ ID NO: 13)
5'-TCGAG-30N-TCCCTATAGTGAGTCGTATTAGCAGCTCCACAGGCT-3'
```

-continued

Forward ligate:
(SEQ ID NO: 14)
5'-UAAUACGACUCACUAUA-3'

Forward primer:
(SEQ ID NO: 15)
5'-AAGCCTGTGGAGCTGCTAATACGACTCACTATAGGGA-3'

Forward bridge:
(SEQ ID NO: 16)
5'-TCCCTATAGTGAGTCGTATTA-NH2-3'

Reverse bridge:
(SEQ ID NO: 17)
5'-TCTTGTTCAGCTTAGTTCTCTCGAG-3'

Reverse ligate:
(SEQ ID NO: 18)
5'-p-GAGAACTAAGCTGAACAAGA-NH2-3'

Human FGF2 (manufactured by Peprotech Inc.) was used as a target substance. FGF2 was immobilized on agarose resin (NHS-activated Sepharose, manufactured by GE Healthcare) by amino coupling. The amino coupling was performed according to the manual of GE Healthcare. The amount of immobilization was confirmed by examining the FGF2 solution before immobilization and the supernatant immediately after immobilization by SDS-PAGE. As a result of SDS-PAGE, FGF2 band was not detected from the supernatant, which confirmed that almost all FGF2 used was coupled. About 290 pmol of FGF2 was immobilized on about 5 µL of resin.

The RNA used in the first round (30N-RNA) was obtained by forming double strand of a chemically synthesized DNA template by using Forward primer and transcribing same using the DuraScribe (trademark) T7 Transcription Kit (manufactured by Epicentre). The RNA obtained by this method has the 2'-position of the ribose of the pyrimidine nucleotide fluoro-substituted. After round 2, double strand DNA was formed, and the 3'-side primer sequence was cleaved by a restriction enzyme, which was followed by transcription.

RNA pool was added to the resin on which FGF2 was immobilized, and the mixture was maintained at room temperature for 1 hr. Thereafter, the resin was washed with solution A to remove RNA not bound to FGF2. Here, solution A is a mixed solution of 145 mM sodium chloride, 5.4 mM potassium chloride, 1.8 mM calcium chloride, 0.8 mM magnesium chloride, 20 mM tris (pH 7.6), and 0.05% Tween 20. The RNA bound to FGF2 was recovered by adding eluent and at 95° C. for 10 min. As eluent, a mixture of 7 M Urea, 3 mM EDTA and 0.1 M tris prepared to pH 6.6 was used. The recovered RNA was amplified by RT-PCR, transcribed using DuraScribe (trademark) T7 Transcription Kit and used as a pool for the next round. With the above as 1 round, a similar operation was performed for 7 rounds. After completion of SELEX, the PCR product was cloned into a pGEM-T Easy vector (manufactured by Promega), which was used to transform Escherichia coli strain DH5α (manufactured by Toyobo). The plasmid was extracted from a single colony and the base sequences of 97 clones were examined by DNA sequencer (3130xl Genetic Analyzer, manufactured by ABI).

After 7 rounds of SELEX, the sequences were examined. Of 89 clones, 79 clones were converged, and could be classified into 11 kinds. The remaining 10 clones were single sequences.

Of the convergent sequences, the binding activity of the nucleic acid shown in SEQ ID NOs: 1 and 2 to FGF2 was evaluated by the surface plasmon resonance method. In the following, the nucleotide sequences shown in SEQ ID NOs: 1 and 2 are shown as aptamer IDs 1 and 2 together with the modification of the 2'-position of ribose. The parentheses in each nucleotide show modifications at the 2'-position of ribose and F is a fluorine atom. Specifically, c(F) is cytidine wherein the 2'-position of ribose is substituted by a fluorine atom, and u(F) is uridine wherein the 2'-position of ribose is substituted by a fluorine atom.

The beginning of each sequence is 5' terminus and the end is 3' terminus.

aptamer ID 1:
GGGAU(F)AC(F)U(F)AGGGC(F)AU(F)U(F)AAU(F)GU(F)U(F)
AC(F)C(F)AGU(F)GU(F)AGU(F)C(F)U(F)C(F)GA aptamer ID 2:
GGGAAAC(F)U(F)AGGGC(F)GU(F)U(F)AAC(F)GU(F)GAC(F)C
(F)AGU(F)GU(F)U(F)U(F)C(F)U(F)C(F)GA For the measurement, BIAcore2000 manufactured by BIAcore was used and, as the sensor chip, CM4 that reacts with an amino group was used. Human FGF2 was dissolved in immobilization solution (10 mM sodium acetate, pH 6) at 25-40 µg/ml. For the reaction of an amino group on the protein side and a carboxyl group on the chip side, ethyl-3-carbodiimide hydrochloride and N-hydroxysuccinimide were used. After the reaction, blocking by ethanolamine-HCl was performed. The immobilized amount of FGF2 was set to 2500-4000 RU. An aptamer for analyte was prepared to 0.15 µM-0.5 µM. As a running buffer, solution A was used. As a regeneration solution, 2M NaCl was used. FGF2 was immobilized on a flow cell $F_c2$, and the results of FC1 were subtracted to give a final sensorgram.

The binding of the 2 sequences was measured to find remarkable binding to FGF2. A sensorgram showing the status of the binding of the aptamer shown by aptamer ID 1 and 2 and human FGF2 is shown in FIG. 1. From the above, it was shown that these nucleic acids are aptamers that bind to FGF2.

Figure 2:
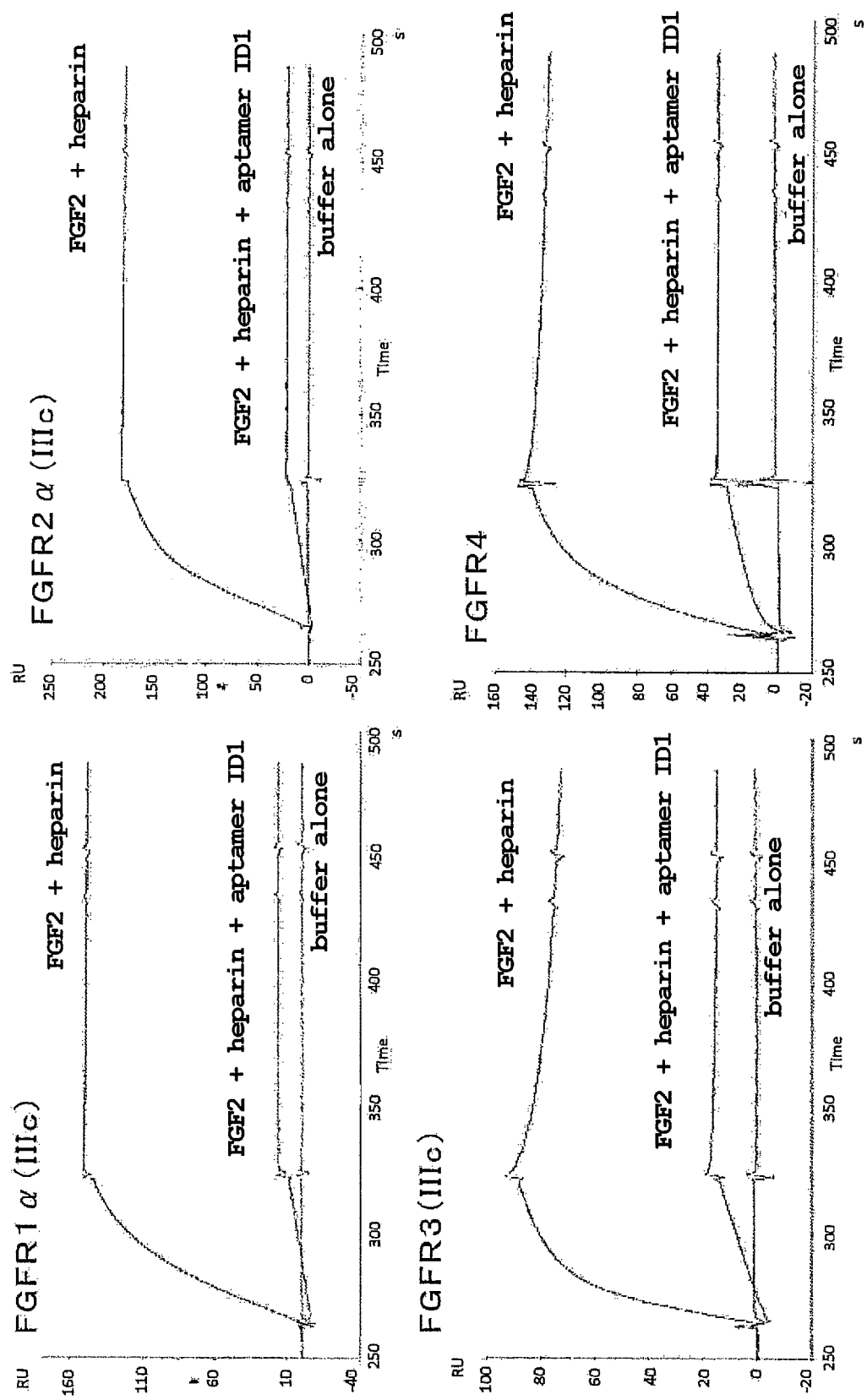
FIG. 2 is a sensorgram showing that the aptamer shown by aptamer ID 1 inhibits binding of human FGF2 and 4 receptors.

Of the 11 clones that showed convergence, 10 clones were selected and whether they inhibit the binding of FGF2 and an FGF2 receptor was examined using the surface plasmon resonance method. BIAcore2000 manufactured by BIAcore was used for the measurement. As directed in BIAcore Company's protocol, Protein A (21181, manufactured by PIERCE) was immobilized on a CM5 sensor chip. About 1,000 RU of human FGFR1α (IIIc), R2α (IIIc), R3 (IIIc), R4 (manufactured by R&D Systems) fused with the Fc portion of IgG (manufactured by R&D systems) was each immobilized thereon. As analyte, a mixture of FGF2 (0.1 µM), heparin (0.1 µM) (manufactured by Pfizer) and aptamer (0.15 µM) was flown. Before an inhibitory test, a mixture of FGF2 and heparin was confirmed to bind to 4 kinds of receptors. As a result of the test, the aptamers shown by aptamer IDs 1 and 2 showed a strong inhibitory activity. A sensorgram showing that the aptamer shown by aptamer ID 1 inhibits binding of FGF2 and FGFR1α(IIIc), 2α(IIIc), 3(IIIc), 4 is shown in FIG. 2.

In addition, the inhibitory rate against each of the 4 kinds of receptors was determined. The inhibitory rate was determined with the maximum binding amount of the FGF2 and heparin mixture as 0, and the binding amount with an injection buffer alone as 100. The binding amount here means the RU value of the peak top of sensorgram. The inhibitory rate was calculated. The aptamers shown by aptamer IDs 1 and 2 showed a high value of not less than 50% for any receptor. The inhibitory rate of other aptamers was not more than 50%. The results thereof are shown in Table 1.

TABLE 1 inhibitory rate of aptamers shown by aptamer IDs 1 and 2 inhibiting binding of human FGF2 and FGF receptor

| | inhibitory rate (%) | | | |
|---|---|---|---|---|
| | FGFR1α (IIIc) | FGFR2α (IIIc) | FGFR3 (IIIc) | FGFR4 |
| aptamer ID 1 | 89% | 88% | 80% | 75% |
| aptamer ID 2 | 89% | 86% | 75% | 73% |

Example 2: Chain Shortening of Aptamers Shown in SEQ ID NOs: 1 and 2

Chain shortening of the aptamers shown in SEQ ID NOs: 1 and 2 was performed. The secondary structure of RNA was predicted using MFOLD program (Zuker, Nucleic Acids Res. 31, 3406-3415, 2003), and chain shortening was performed by reference to the structure. A chain-shortened form was obtained by producing DNA of the object sequence by chemical synthesis, and transcription thereof using DuraScribe T7 Transcription Kit. In the following, the nucleotide sequences (SEQ ID NOs: 3 and 7) in a chain-shortened form actually produced are shown as aptamer IDs 3 and 7 together with the modification of the 2'-position of ribose.

aptamer ID 3: aptamer of 36 nucleotides in length which is altered from the aptamer shown in SEQ ID NO: 1

GGGAU(F)AC(F)U(F)AGGGC(F)AU(F)U(F)AAU(F)GU(F)U(F)A

C(F)C(F)AGU(F)GU(F)AGU(F)C(F)C(F)C(F)

aptamer ID 7: aptamer of 35 nucleotides in length which is altered from the aptamer shown in SEQ ID NO: 2

GGGAAAC(F)U(F)AGGGC(F)GU(F)U(F)AAC(F)GU(F)GAC(F)C (F)AGU(F)GU(F)U(F)U(F)C(F)C(F)C(F)

Whether these nucleic acids have a binding activity to FGF2 was examined by the surface plasmon resonance method as in Example 1. The results thereof are shown in Table 2. The aptamers shown by aptamer IDs 3 and 7 was found to markedly bind to FGF2. In addition, whether the aptamers have a binding inhibitory activity against the binding of FGF2 and an FGF2 receptor was examined by the surface plasmon resonance method in the same manner as in Example 1 to find that the aptamers shown by aptamer IDs 3 and 7 show high inhibition.

TABLE 2 inhibitory rate of aptamers shown by aptamer IDs 3 and 7 inhibiting binding of human FGF2 and FGF receptor

| | FGFR1α (IIIc) |
|---|---|
| aptamer ID 3 | 89% |
| aptamer ID 7 | 85% |

Example 3: Specificity of Aptamer Shown by Aptamer ID 3

Figure 3:
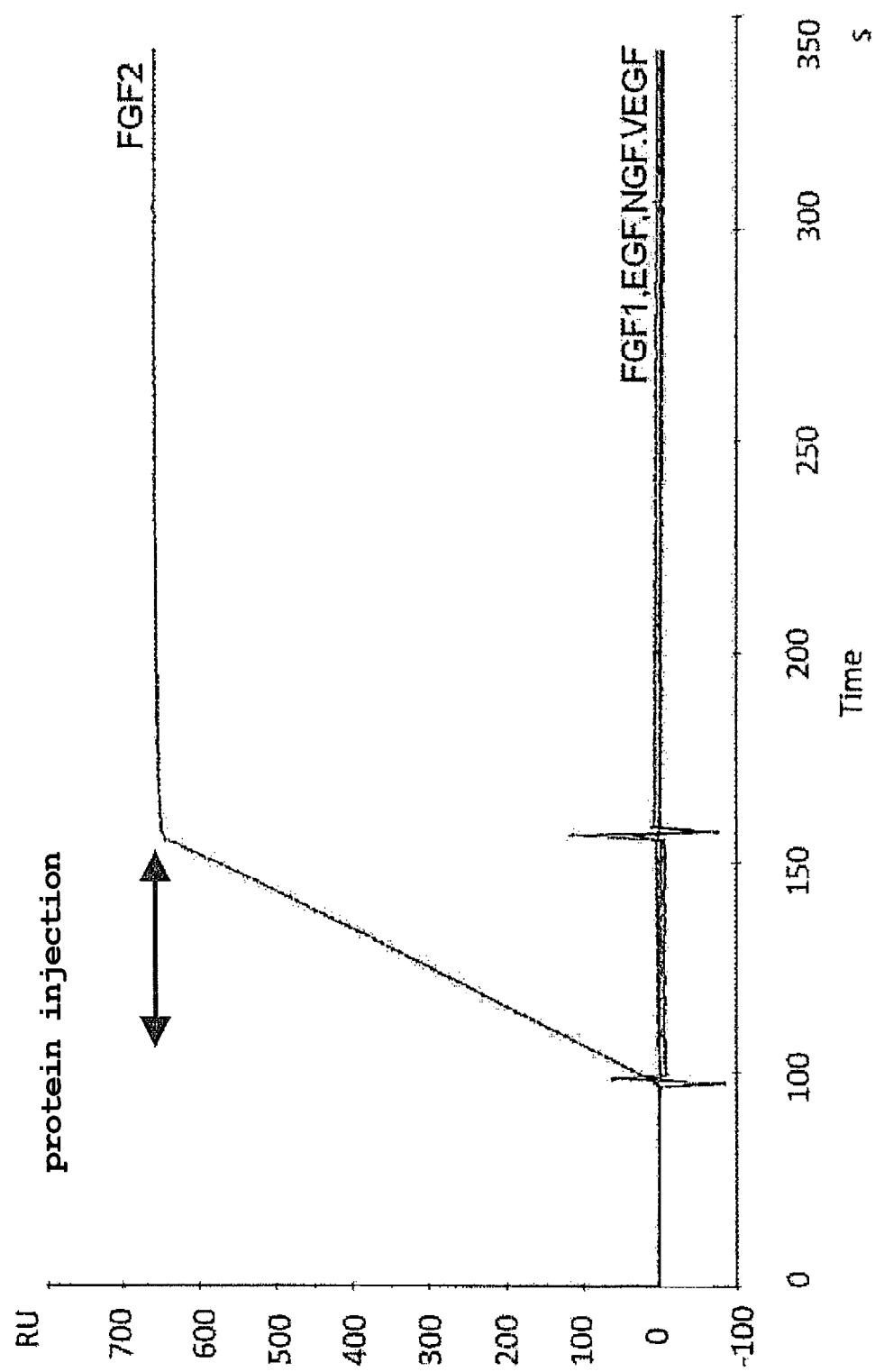
FIG. 3 is a sensorgram showing that the aptamer shown by aptamer ID 3 does not bind to human FGF1, EGF, NGF, VEGF.

Whether FGF2 aptamer shown by aptamer ID 3 binds to FGF1 in the same FGF family, or some growth factors EGF, β-NGF, VEGF was examined by the surface plasmon resonance method. The measurements were taken using BIAcore 2000 manufactured by BIAcore. The SA chip was used as the sensor chip, which had streptavidin immobilized thereon. Bound thereto was about 500 RU of the aptamer shown by aptamer ID 3 added with biotin to the 5 terminal. The biotin-added aptamer was produced by chemical synthesis. As the protein to be the ligand, FGF1, EGF, β-NGF, VEGF manufactured by R&D were used. As a running buffer, solution A used in Example 1 added with sodium chloride to a final concentration of 0.3 M was used. As a result, it was found that the aptamer shown by aptamer ID 3 binds to FGF2, but does not bind to other proteins. The sensorgram thereof is shown in FIG. 3.

From the above, it was found that the aptamer shown by aptamer ID 3 specifically binds to FGF2.

Example 4: Alteration and Modification of Chain-Shortened Aptamer

To enhance FGF2-binding activity, stability, drug deliverability and the like, the nucleic acids shown by aptamer IDs 3(1)-3(40), aptamer IDs 4 and 4(1)-4(4), aptamer ID 5 and aptamer ID 6 were chemically synthesized based on the aptamer shown in SEQ ID NO: 3. Here, the aptamer shown by aptamer ID 4 is the aptamer shown by aptamer ID 3(19) wherein one G(M) at the 5'-terminal and one C(M) at the 3'-terminal have been deleted. The aptamer shown by aptamer ID 5 is the aptamer shown by aptamer ID 3(19) wherein one G(M) has been added at the 5'-terminal and one C(M) has been added at the 3'-terminal. The aptamer shown by aptamer ID 6 is the aptamer shown by aptamer ID 3(19) wherein A(M) alone has been added at the 5'-terminal. These nucleic acids were produced by chemical synthesis. Whether the produced aptamers inhibit the binding of FGF2 and an FGF2 receptor was examined in the same manner as in Example 1. As used herein, the concentration of aptamer, FGF2, heparin was 0.1 μM. As a result of the experiment, it was found that all measured aptamers strongly inhibited the binding of FGF2 and FGFR1α (IIIc) receptor. The results thereof are shown in Table 3.

TABLE 3 inhibitory rate of aptamers inhibiting binding of FGF2 and FGFR1α (IIIc) receptor in the presence of heparin

| | inhibitory rate (%) |
|---|---|
| aptamer ID 3(1) | 84 |
| aptamer ID 3(2) | 89 |
| aptamer ID 3(3) | 87 |
| aptamer ID 3(4) | 89 |
| aptamer ID 3(5) | 87 |
| aptamer ID 3(6) | 78 |
| aptamer ID 3(7) | 89 |
| aptamer ID 3(8) | 84 |
| aptamer ID 3(9) | 89 |
| aptamer ID 3(10) | 89 |
| aptamer ID 3(11) | 88 |
| aptamer ID 3(12) | 89 |
| aptamer ID 3(13) | 88 |
| aptamer ID 3(14) | 87 |
| aptamer ID 3(15) | 86 |
| aptamer ID 3(16) | 87 |

TABLE 3-continued inhibitory rate of aptamers inhibiting binding of FGF2 and
FGFR1α (IIIc) receptor in the presence of heparin

| | inhibitory rate (%) |
|---|---|
| aptamer ID 3(17) | 88 |
| aptamer ID 3(18) | 89 |
| aptamer ID 3(19) | 93 |
| aptamer ID 3(20) | 96 |
| aptamer ID 3(21) | 97 |
| aptamer ID 3(22) | 98 |
| aptamer ID 3(23) | 91 |
| aptamer ID 3(24) | 90 |
| aptamer ID 3(25) | 90 |
| aptamer ID 3(26) | 99 |
| aptamer ID 3(27) | 99 |
| aptamer ID 3(28) | 91 |
| aptamer ID 3(29) | 91 |
| aptamer ID 3(30) | 99 |
| aptamer ID 3(31) | 91 |
| aptamer ID 3(32) | 91 |
| aptamer ID 3(33) | 90 |
| aptamer ID 3(34) | 91 |
| aptamer ID 3(35) | 84 |
| aptamer ID 3(36) | 98 |
| aptamer ID 3(37) | 97 |
| aptamer ID 3(38) | 97 |
| aptamer ID 3(39) | 97 |
| aptamer ID 3(40) | 97 |
| aptamer ID 4 | 95 |
| aptamer ID 4(1) | 93 |
| aptamer ID 4(2) | 94 |
| aptamer ID 4(3) | 96 |
| aptamer ID 4(4) | 96 |
| aptamer ID 5 | 94 |
| aptamer ID 6 | 93 |

From the above, it was shown that all aptamers shown by the aforementioned aptamer IDs have a high inhibitory activity against the binding of FGF2 and an FGF receptor.

Respective sequences are shown below. Capital letter shows RNA, small letter shows DNA, and idT shows inverted dT. The parenthesis in each nucleotide shows modification at the 2'-position thereof, F shows a fluorine atom, and M shows an 0-methyl group. s shows a phosphorothioate bond. C6 shows —(CH$_2$)$_6$-linker, and ssH shows ssH Linker (—CH$_2$—CH$_2$—O—CO—NH—(CH$_2$)$_6$—). PEG40TS2 is 2-branched TS type polyethylene glycol having a molecular weight of 40000 (SUNBRIGHT GL2-400TS manufactured by NOF CORPORATION), PEG80TS4 is 4-branched TS type PEG having a molecular weight of 80000 (SUNBRIGHT GL4-800TS manufactured by NOF CORPORATION), Y-NHS-40K is Y-Shape PEG NHS Esyer (Y-NHS-40K manufactured by JenKem Technology USA) having a molecular weight of 40000, ME-100TS is TS type (SUNBRIGHT ME-100TS manufactured by NOF CORPORATION) having a molecular weight of 10000, and PTE-100CS is 4 branched type (SUNBRIGHT PTE-100CS manufactured by NOF CORPORATION) having a molecular weight of 10000. The nucleotide sequences of aptamer IDs 3(1)-(40) free of linker moiety and modified moiety are each shown in SEQ ID NO: 3, and similarly, the nucleotide sequences of aptamer IDs 4 and 4(1)-(4), aptamer IDs 5 and 6 are each represented by SEQ ID NOs: 4-6.

```
aptamer ID 3(1)
GGGAU(F)AC(F)U(F)AGGGC(F)A(M)U(F)U(F)A(M)A(M)U(F)G (M)U(F)U(F)AC(F)C(F)AGU(F)GU(F)AGU(F)C(F)C(F)C(F)

aptamer ID 3(2)
G(M)G(M)G(M)A(M)U(F)AC(F)U(F)AGGGC(F)AU(F)U(F)AAU (F)GU(F)U(F)AC(F)C(F)AGU(F)GU(F)AGU(F)C(F)C(F)C(F)

aptamer ID 3(3)
GGGAU(F)AC(F)U(F)AGG(M)GC(F)AU(F)U(F)AAU(F)GU(F)U (F)AC(F)C(F)AGU(F)GU(F)AGU(F)C(F)C(F)C(F)

aptamer ID 3(4)
GGGAU(F)AC(F)U(F)AG(M)GGC(F)AU(F)U(F)AAU(F)GU(F)U (F)AC(F)C(F)AGU(F)GU(F)AGU(F)C(F)C(F)C(F)

aptamer ID 3(5)
GGGAU(F)AC(F)U(F)A(M)GGGC(F)AU(F)U(F)AAU(F)GU(F)U (F)AC(F)C(F)AGU(F)GU(F)AGU(F)C(F)C(F)C(F)

aptamer ID 3(6)
GGGAU(F)AC(F)U(F)AGGGC(F)AU(F)U(F)AAU(F)GU(F)U(F)A (M)C(F)C(F)AGU(F)GU(F)AGU(F)C(F)C(F)C(F)

aptamer ID 3(7)
GGGAU(F)AC(F)U(F)AGGGC(F)AU(F)U(F)AAU(F)GU(F)U(F)

AC(F)C(F)A(M)GU(F)GU(F)AGU(F)C(F)C(F)C(F)

aptamer ID 3(8)
G(M)G(M)G(M)A(M)U(F)AC(F)U(F)A(M)G(M)G(M)GC(F)A(M)

U(F)U(F)A(M)A(M)U(F)G(M)U(F)U(F)A(M)C(F)C(F)A(M)GU (F)GU(F)AGU(F)C(F)C(F))C(F)-idT aptamer ID 3(9)
GGGAU(F)A(M)C(F)U(F)AGGGC(F)AU(F)U(F)AAU(F)GU(F)U (F)AC(F)C(F)AGU(F)GU(F)AGU(F)C(F)C(F)C(F)

aptamer ID 3(10)
GGGAU(F)AC(F)U(F)AGGGC(F)AU(F)U(F)AAU(F)GU(F)U(F)A

C(F)C(F)AGU(F)GU(F)AG(M)U(F)C(F)C(F)C(F)

aptamer ID 3(11)
GGGAU(F)AC(F)U(F)AGGGC(F)AU(F)U(F)AAU(F)GU(F)U(F)A

C(F)C(F)AGU(F)GU(F)A(M)GU(F)C(F)C(F)C(F)

aptamer ID 3(12)
G(M)G(M)G(M)A(M)U(F)AC(F)U(F)A(M)G(M)G(M)GC(F)A(M)

U(F)U(F)A(M)A(M)U(F)G(M)U(F)U(F)A(M)C(F)C(F)A(M)GU (F)GU(F)AGU(M)C(M)C(M)C(M)-idT aptamer ID 3(13)
G(M)G(M)G(M)A(M)U(F)AC(F)U(F)A(M)G(M)G(M)GC(F)A(M)

U(M)U(M)A(M)U(M)G(M)U(F)U(F)A(M)C(F)C(F)A(M)GU (F)GU(F)AGU(F)C(F)C(F)C(F)

aptamer ID 3(14)
G(M)G(M)G(M)A(M)U(F)AC(F)U(F)A(M)G(M)G(M)GC(F)A(M)

U(F)U(F)A(M)A(M)U(F)G(M)U(F)U(M)A(M)C(F)C(F)A(M)GU (F)GU(F)AGU(F)C(F)C(F)C(F)

aptamer ID 3(15)
G(M)G(M)G(M)A(M)U(F)AC(F)U(F)A(M)G(M)G(M)GC(F)A(M)

U(F)U(F)A(M)A(M)U(F)G(M)U(F)U(F)A(M)C(M)C(M)A(M)GU (F)GU(F)AGU(F)C(F)C(F)C(F)
```

-continued aptamer ID 3(16)
G(M)G(M)G(M)A(M)U(M)AC(F)U(F)A(M)G(M)G(M)GC(F)A(M)
U(F)U(F)A(M)A(M)U(F)G(M)U(F)U(F)A(M)C(F)C(F)A(M)GU
(F)GU(F)AGU(F)C(F)C(F)C(F)

aptamer ID 3(17)
G(M)G(M)G(M)A(M)U(M)AC(F)U(F)A(M)G(M)G(M)GC(F)A(M)
U(F)U(F)A(M)A(M)U(F)G(M)U(F)U(F)A(M)C(F)C(F)A(M)GU
(F)GU(F)AGU(F)C(F)C(F)C(F)

aptamer ID 3(18)
G(M)G(M)G(M)A(M)U(M)A(M)C(M)U(F)A(M)G(M)G(M)GC(M)A
(M)U(M)U(F)A(M)A(M)U(M)G(M)U(F)U(M)A(M)C(M)C(M)A
(M)GU(F)GU(F)A(M)G(M)U(M)C(M)C(M)C(M)

aptamer ID 3(19)
G(M)G(M)G(M)A(M)U(M)A(M)C(M)U(F)A(M)G(M)G(M)GC(M)A
(M)U(M)U(F)A(M)A(M)U(M)G(M)U(F)U(M)A(M)C(M)C(M)A
(M)GU(F)GU(F)A(M)G(M)U(M)C(M)C(M)C(M)-idT aptamer ID 3(20)
idT-G(M)G(M)G(M)A(M)U(M)A(M)C(M)U(F)A(M)G(M)G(M)GC
(M)A(M)U(M)U(F)A(M)A(M)U(M)G(M)U(F)U(M)A(M)C
(M)A(M)GU(F)GU(F)A(M)G(M)U(M)C(M)C(M)C(M)

aptamer ID 3(21)
GL2-400TS-C6-G(M)G(M)G(M)A(M)U(M)A(M)C(M)U(F)A(M)G
(M)G(M)GC(M)A(M)U(M)U(F)A(M)A(M)U(M)G(M)U(F)U(M)A
(M)C(M)C(M)A(M)GU(F)GU(F)A(M)G(M)U(M)C(M)C(M)C(M)-
idT aptamer ID 3(22)
idT-G(M)G(M)G(M)A(M)U(M)A(M)C(M)U(F)A(M)G(M)G(M)GC
(M)A(M)U(M)U(F)A(M)A(M)U(M)G(M)U(F)U(M)A(M)C(M)C
(M)A(M)GU(F)GU(F)A(M)G(M)U(M)C(M)C(M)C(M)-C6-GL2-
400TS aptamer ID 3(23)
G(M)G(M)G(M)A(M)U(M)A(M)C(M)U(F)A(M)G(M)G(M)gC(M)A
(M)U(M)U(F)A(M)A(M)U(M)G(M)U(F)U(M)A(M)C(M)C(M)A
(M)GU(F)GU(F)A(M)G(M)U(M)C(M)C(M)C(M)

aptamer ID 3(24)
G(M)G(M)G(M)A(M)U(M)A(M)C(M)U(F)A(M)G(M)G(M)GC(M)A
(M)U(M)U(F)A(M)A(M)U(M)G(M)U(F)U(M)A(M)C(M)C(M)A
(M)gU(F)GU(F)A(M)G(M)U(M)C(M)C(M)C(M)

aptamer ID 3(25)
G(M)G(M)G(M)A(M)U(M)A(M)C(M)U(F)A(M)G(M)G(M)G(F)C
(M)A(M)U(M)U(F)A(M)A(M)U(M)G(M)U(F)U(M)A(M)C
(M)A(M)GU(F)GU(F)A(M)G(M)U(M)C(M)C(M)C(M)

aptamer ID 3(26)
G(M)G(M)G(M)A(M)U(M)U(F)A(M)G(M)G(M)GC(M)A
(M)U(M)U(F)A(M)A(M)U(M)G(M)U(F)U(M)A(M)C(M)C(M)A
(M)G(F)U(F)GU(F)A(M)G(M)U(M)C(M)C(M)C(M)

aptamer ID 3(27)
G(M)G(M)G(M)A(M)U(M)A(M)C(M)U(F)A(M)G(M)G(M)GC(M)A
(M)U(M)U(F)A(M)A(M)U(M)G(M)U(F)U(M)A(M)C(M)C(M)A
(M)GU(F)G(F)U(F)A(M)G(M)U(M)C(M)C(M)C(M)

aptamer ID 3(28)
G(M)G(M)G(M)A(M)U(M)A(M)C(M)U(F)A(M)G(M)G(M)sGC(M)
A(M)U(M)U(F)A(M)A(M)U(M)G(M)U(F)U(M)A(M)C(M)C(M)A
(M)GU(F)GU(F)A(M)G(M)U(M)C(M)C(M)C(M)

aptamer ID 3(29)
G(M)G(M)G(M)A(M)U(M)A(M)C(M)U(F)A(M)G(M)G(M)GsC(M)
A(M)U(M)U(F)A(M)A(M)U(M)G(M)U(F)U(M)A(M)C(M)C(M)A
(M)GU(F)GU(F)A(M)G(M)U(M)C(M)C(M)C(M)

aptamer ID 3(30)
G(M)G(M)G(M)A(M)U(M)A(M)C(M)U(F)A(M)G(M)G(M)GC(M)A
(M)U(M)U(F)A(M)A(M)U(M)G(M)U(F)U(M)A(M)C(M)C(M)A
(M)sGU(F)GU(F)A(M)G(M)U(M)C(M)C(M)C(M)

aptamer ID 3(31)
G(M)G(M)G(M)A(M)U(M)A(M)C(M)U(F)A(M)G(M)G(M)GC(M)A
(M)U(M)U(F)A(M)A(M)U(M)G(M)U(F)U(M)A(M)C(M)C(M)A
(M)GsU(F)GU(F)A(M)G(M)U(M)C(M)C(M)C(M)

aptamer ID 3(32)
G(M)G(M)G(M)A(M)U(M)A(M)C(M)U(F)A(M)G(M)G(M)GC(M)A
(M)U(M)U(F)A(M)A(M)U(M)G(M)U(F)U(M)A(M)C(M)C(M)A
(M)GU(F)sGU(F)A(M)G(M)U(M)C(M)C(M)C(M)

aptamer ID 3(33)
G(M)G(M)G(M)A(M)U(M)A(M)C(M)U(F)A(M)G(M)G(M)GC(M)A
(M)U(M)U(F)A(M)A(M)U(M)G(M)U(F)U(M)A(M)C(M)C(M)A
(M)GU(F)GsU(F)A(M)G(M)U(M)C(M)C(M)C(M)

aptamer ID 3(34)
G(M)G(M)G(M)A(M)U(M)A(M)C(M)U(F)A(M)G(M)G(M)G(F)C
(M)A(M)U(M)U(F)A(M)A(M)U(M)G(M)U(F)U(M)A(M)C
(M)A(M)G(F)U(F)G(F)U(F)A(M)G(M)U(M)C(M)C(M)C(M)-
idT aptamer ID 3(35)
G(M)G(M)G(M)A(M)U(M)A(M)C(M)U(F)A(M)G(M)G(M)G(F)C
(M)A(M)U(M)U(F)A(M)A(M)U(M)G(M)U(F)U(M)A(M)C
(M)A(M)G(F)U(F)GU(F)A(M)G(M)U(M)C(M)C(M)C(M)-idT aptamer ID 3(36)
GL4-800TS-C6-G(M)G(M)G(M)A(M)U(M)A(M)C(M)U(F)A(M)G
(M)G(M)GC(M)A(M)U(M)U(F)A(M)A(M)U(M)G(M)U(F)U(M)A
(M)C(M)C(M)A(M)GU(F)GU(F)A(M)G(M)U(M)C(M)C(M)C(M)-
idT -continued aptamer ID 3(37)
Y-NHS-40K-ssH-G(M)G(M)G(M)A(M)U(M)A(M)C(M)U(F)A(M)
G(M)G(M)GC(M)A(M)U(M)U(F)A(M)A(M)U(M)G(M)U(F)U(M)A
(M)C(M)C(M)A(M)GU(F)GU(F)A(M)G(M)U(M)C(M)C(M)C(M)-
idT aptamer ID 3(38)
ME-100TS-C6-G(M)G(M)G(M)A(M)U(M)A(M)C(M)U(F)A(M)G
(M)G(M)GC(M)A(M)U(M)U(F)A(M)A(M)U(M)G(M)U(F)U(M)A
(M)C(M)C(M)A(M)GU(F)GU(F)A(M)G(M)U(M)C(M)C(M)C(M)-
idT aptamer ID 3(39)
PTE-100CS-C6-G(M)G(M)G(M)A(M)U(M)A(M)C(M)U(F)A(M)G
(M)G(M)GC(M)A(M)U(M)U(F)A(M)A(M)U(M)G(M)U(F)U(M)A
(M)C(M)C(M)A(M)GU(F)GU(F)A(M)G(M)U(M)C(M)C(M)C(M)-
idT aptamer ID 3(40)
GL2-400TS-ssH-G(M)G(M)G(M)A(M)U(M)A(M)C(M)U(F)A(M)
G(M)G(M)GC(M)A(M)U(M)U(F)A(M)A(M)U(M)G(M)U(F)U(M)A
(M)C(M)C(M)A(M)GU(F)GU(F)A(M)G(M)U(M)C(M)C(M)C(M)-
idT aptamer ID 4: altered form of aptamer shown by
aptamer ID 3(19) and having a length of 34
nucleotides
G(M)G(M)A(M)U(M)A(M)C(M)U(F)A(M)G(M)G(M)GC(M)A(M)U
(M)U(F)A(M)A(M)U(M)G(M)U(F)U(M)A(M)C(M)C(M)A(M)GU
(F)GU(F)A(M)G(M)U(M)C(M)C(M)-idT aptamer ID 4(1)
G(M)G(M)A(M)U(M)A(M)C(M)U(F)A(M)G(M)G(M)G(F)C(M)A
(M)U(M)U(F)A(M)A(M)U(M)G(M)U(F)U(M)A(M)C(M)C(M)A
(M)GU(F)GU(F)A(M)G(M)U(M)C(M)C(M)-idT aptamer ID 4(2)
G(M)G(M)A(M)U(M)A(M)C(M)U(F)A(M)G(M)G(M)G(F)C(M)A
(M)U(M)U(F)A(M)A(M)U(M)G(M)U(F)U(M)A(M)C(M)C(M)A
(M)G(F)U(F)GU(F)A(M)G(M)U(M)C(M)C(M)-idT aptamer ID 4(3)
G(M)G(M)A(M)U(M)A(M)C(M)U(F)A(M)G(M)G(M)G(F)C(M)A
(M)U(M)U(F)A(M)A(M)U(M)G(M)U(F)U(M)A(M)C(M)C(M)A
(M)GU(F)sGU(F)A(M)G(M)U(M)C(M)C(M)-idT aptamer ID 4(4)
G(M)G(M)A(M)U(M)A(M)C(M)U(F)A(M)G(M)G(M)G(F)C(M)A
(M)U(M)U(F)A(M)A(M)U(M)G(M)U(F)U(M)A(M)C(M)C(M)A
(M)G(F)U(F)GsU(F)A(M)G(M)U(M)C(M)C(M)-idT aptamer ID 5: altered form of aptamer shown by
aptamer ID 3(19) and having a length of 38
nucleotides
G(M)G(M)G(M)G(M)A(M)U(M)A(M)C(M)U(F)A(M)G(M)G(M)GC
(M)A(M)U(M)U(F)A(M)A(M)U(M)G(M)U(F)U(M)A(M)C(M)C
(M)A(M)GU(F)GU(F)A(M)G(M)U(M)C(M)C(M)C(M)-idT aptamer ID 6: altered form of aptamer shown by
aptamer ID 3(19) and having a length of 37
nucleotides
A(M)G(M)G(M)G(M)A(M)U(M)A(M)C(M)U(F)A(M)G(M)G(M)GC
(M)A(M)U(M)U(F)A(M)A(M)U(M)G(M)U(F)U(M)A(M)C(M)C
(M)A(M)GU(F)GU(F)A(M)G(M)U(M)C(M)C(M)C(M)-idT Example 5: Evaluation of FGF2 Dependent Cell Proliferation Inhibitory Activity of Aptamer by Using Human Umbilical Vein Endothelial Cells Human umbilical vein endothelial cells (HUVEC) were seeded in a 96 well flat bottom plate at $5 \times 10^3$ cells per well, and cultured overnight using a medium EGM-2 Bullet Kit for endothelial cells (CC-3162 manufactured by Lonza) containing 2% fetal bovine serum and growth factors. Thereafter, the medium was discarded, the cells were washed twice with PBS buffer, and a mixture of the aptamer shown by aptamer ID 3(21) (5, 2.5, 1, 0.5 nM) and FGF2 (final concentration 0.5 nM), dissolved in a medium exclusively for endothelial cells containing 2% fetal bovine serum, was added. After 72 hr, viable cell number was examined using Cell Counting Kit-8. For the measurement of absorbance, a microplate reader (450 nm) was used. One sample was measured at n=3. As a positive control, anti-FGF2 antibody Anti-FGF, basic (Ab-3) Mouse mAb (3H3) (manufactured by Calbiochem) were used. With the OD value per well obtained by the addition of FGF2 alone and culture of the cells for 3 days as inhibitory activity 0%, and that of the cell obtained by FGF2 free culture for 3 days as inhibitory activity 100%, the inhibitory activity of the aptamer was calculated from the OD value per well obtained by culturing with the addition of a mixture of FGF2 and the aptamer. As a result, it was shown that the aptamer shown by aptamer ID 3(21) has a high inhibitory activity against FGF2. The IC50 value was about 1.0 nM. The results are shown in Table 4.

TABLE 4 suppression of growth of HUVEC cells by aptamer shown by aptamer ID 3(21) with addition of FGF2

|  | inhibitory rate (%) |
| --- | --- |
| — | 100 |
| FGF2 (500 pM) | 0 |
| 3H3 (25 nM) + FGF2 (500 pM) | 100 |
| 3H3 (5 nM) + FGF2 (500 pM) | 30 |
| 3H3 (1 nM) + FGF2 (500 pM) | 8.5 |
| aptamer ID 3(21) (5 nM) + FGF2 (500 pM) | 100 |
| aptamer ID 3(21) (2.5 nM) + FGF2 (500 pM) | 86 |
| aptamer ID 3(21) (1 nM) + FGF2 (500 pM) | 47 |
| aptamer ID 3(21) (0.5 nM) + FGF2 (500 pM) | 0 |
| scramble sequence (5 nM) + FGF2 (500 pM) | 11 |

"—" means without addition of FGF2.

From the above, it was suggested that the aptamer shown by aptamer ID 3(21) inhibits angiogenesis.

By a method similar to the above except that the 96 well flat bottom plate was changed to a collagen-coated one, the activity of various aptamers was evaluated. The concentration of FGF2 added was 0.58 nM. The results thereof are shown in Table 5. As a negative control RNA, Macugen (registered trade mark) sequence without addition of PEG, and with C6 modification of the 5'-terminal and idT modification of the 3'-terminal was used.

TABLE 5

IC50 value of aptamer suppressing growth of HUVEC cells with addition of FGF2

| aptamer ID | IC50 (nM) |
|---|---|
| 3(8) | 27 |
| 3(12) | 21 |
| 3(13) | 15 |
| 3(14) | 12 |
| 3(15) | 14 |
| 3(16) | 7.9 |
| 3(18) | 2.6 |
| 3(23) | 5.3 |
| 3(24) | 7.3 |
| 3(25) | 5.1 |
| 3(26) | 3.0 |
| 3(27) | 3.7 |
| 3(28) | 4.0 |
| 3(29) | 3.1 |
| 3(30) | 3.3 |
| 3(31) | 10 |
| 3(32) | 4.0 |
| 3(33) | 4.0 |
| 4 | 5.0 |
| 4(1) | 3.8 |
| 4(2) | 5.1 |
| 4(3) | 4.6 |
| 4(4) | 4.5 |
| 5 | 2.6 |
| 6 | 3.1 |
| negative control RNA | >400 |

From the above, it was suggested that the aptamers shown by the above-mentioned aptamer IDs similarly inhibit angiogenesis.

Example 6: Evaluation of FGF2 Dependent Cell Proliferation Inhibitory Activity of Aptamer by Using Human Umbilical Vein Endothelial Cells-2

By a method similar to that in Example 5, the inhibitory activity of the aptamers shown by aptamer IDs 8-12 was measured. The results thereof are shown in Table 6.

The nucleotide sequences of aptamer IDs 8-12 are shown in SEQ ID NOs: 8-12, respectively.

aptamer ID 8
NH2-C(M)G(M)G(M)A(M)U(M)A(M)C(M)U(F)A(M)G(M)G(M)GC(M)A(M)U(M)U(F)A(M)A(M)U(M)G(M)U(F)U(M)A(M)C(M)C(M)A(M)GU(F)GU(F)A(M)G(M)U(M)C(M)C(M)G(M)-idT aptamer ID 9
NH2-C(M)C(M)G(M)A(M)U(M)A(M)C(M)U(F)A(M)G(M)G(M)GC(M)A(M)U(M)U(F)A(M)A(M)U(M)G(M)U(F)U(M)A(M)C(M)C(M)A(M)GU(F)GU(F)A(M)G(M)U(M)C(M)G(M)G(M)-idT aptamer ID 10
G(M)G(M)G(M)A(M)U(M)A(M)C(M)U(F)A(M)G(M)G(M)GC(M)G(M)U(M)U(F)A(M)A(M)C(M)G(M)U(F)U(M)A(M)C(M)C(M)A(M)GU(F)GU(F)A(M)G(M)U(M)C(M)C(M)C(M)

aptamer ID 11
G(M)G(M)G(M)A(M)U(M)A(M)C(M)U(F)A(M)G(M)G(M)GC(M)C(M)U(M)U(F)A(M)A(M)G(M)G(M)U(F)U(M)A(M)C(M)C(M)A(M)GU(F)GU(F)A(M)G(M)U(M)C(M)C(M)C(M)

aptamer ID 12
G(M)G(M)G(M)A(M)U(M)A(M)C(M)U(F)A(M)G(M)G(M)GC(M)A(M)U(M)U(F)U(M)A(M)U(M)G(M)U(F)U(M)A(M)C(M)C(M)A(M)GU(F)GU(F)A(M)G(M)U(M)C(M)C(M)C(M)

TABLE 6

IC50 value of aptamer suppressing growth of HUVEC cells with addition of FGF2

| aptamer ID | IC50 (nM) |
|---|---|
| aptamer ID 8 | 5.6 |
| aptamer ID 9 | 3.7 |
| aptamer ID 10 | 4.9 |
| aptamer ID 11 | 13 |
| aptamer ID 12 | 2.3 |
| aptamer ID 3(19) | 3.4 |

Example 7: Angiogenesis Mouse Model Test 0.76% (final concentration) sodium citrate-containing Matrigel (BD Matrigel™) containing human FGF-2 (manufactured so by R&D) was subcutaneously injected to 8-week-old C57BL/6J mouse (female) under anesthesia. After 7 days, Matrigel was isolated, and the level of angiogenesis was evaluated based on the level of hemoglobin in the Matrigel. The hemoglobin level was quantified by the cyanmethemoglobin method by using Drabkin Reagent Kit. The aptamer was dissolved in a phosphate buffer containing 1 mM magnesium chloride, and intraperitoneally administered once per day from immediately after the subcutaneous administration of Matrigel. The administration group is shown in Table 7, and the results are shown in Table 8. Remarkable inhibition of angiogenesis was observed in aptamer 1 mg/kg group. From the above, it was confirmed that the aptamer of the present invention also shows a strong angiogenesis inhibitory activity in the animal model.

TABLE 7 explanation of administration group

| | administration group | FGF-2 (μg) | aptamer dose (mg/kg) | administration route | administration frequency | animal number (mouse) |
|---|---|---|---|---|---|---|
| 1 | control group | 0 | 0 | intra-peritoneal | once per day | 3 |
| 2 | solvent administration group | 1 | 0 | intra-peritoneal | once per day | 3 |
| 3 | aptamer ID 3(22) low dose group | 1 | 0.1 | intra-peritoneal | once per day | 3 |
| 4 | aptamer ID 3(22) high dose group | 1 | 1 | intra-peritoneal | once per day | 3 |

TABLE 8 results of angiogenesis mouse model test

| | administration group | hemoglobin amount (mg/mL) |
|---|---|---|
| 1 | control group | 0.19 |
| 2 | solvent administration group | 2.2 |

TABLE 8-continued results of angiogenesis mouse model test

| administration group | hemoglobin amount (mg/mL) |
|---|---|
| 3  aptamer ID 3(22) low dose group | 1.3 |
| 4  aptamer ID 3(22) high dose group | 0.29 |

This application is based on patent application No. 2014-60966 (filing date: Mar. 24, 2014) filed in Japan, the contents of which are encompassed in full herein.

INDUSTRIAL APPLICABILITY

The aptamer or complex of the present invention can be useful as a medicament, or a diagnostic agent or a reagent for diseases such as a disease accompanied by angiogenesis, bone•articular disease, pain and the like. The aptamer and complex of the present invention can also be useful for the purification and concentration of FGF2, labeling of FGF2, as well as detection and quantification of FGF2.

The invention claimed is:

1. An aptamer that binds to FGF2, which comprises the nucleotide sequence of formula (1) wherein uracil is optionally thymine, and which is the following (a) or (b):

$N^1$GGA$N^2$ACUAGGGC$N^3$UUA-A$N^4$GU$N^5$ACCAGUGU$N^6$  (formula 1) (SEQ ID NO:19)

$N^1$ and $N^6$ are each independently any 0 to several bases, $N^2$, $N^3$, $N^4$ and $N^5$ are independently any one base, (a) an aptamer wherein, in the nucleotides contained in the aptamer,
  (i) the 2'-position of the ribose of each pyrimidine nucleotide is a fluorine atom,
  (ii) the 2'-position of the ribose of each purine nucleotide is a hydroxy group;

(b) the aptamer of (a), wherein
  (i) the fluorine atom at the 2'-position of the ribose of each pyrimidine nucleotide is independently unsubstituted, or substituted by an atom or group selected from the group consisting of a hydrogen atom, a hydroxy group and a methoxy group,
  (ii) the hydroxy group at the 2'-position of the ribose of each purine nucleotide is independently unsubstituted, or substituted by an atom or group selected from the group consisting of a hydrogen atom, a methoxy group and a fluorine atom.

2. The aptamer according to claim 1, wherein
$N^1$ is G, GG, AG, C or gap,
$N^2$ is A or U,
$N^3$ is G, C or A,
$N^4$ is G, C or U,
$N^5$ is G or U, and
$N^6$ is UUC$N^{61}$ or AGUC$N^{62}$ wherein $N^{61}$ and $N^{62}$ are each independently any 0 to several bases.

3. The aptamer according to claim 1, comprising the nucleotide sequence of formula (2) or (3):

GGGAAACUAGGGCGUUAACGUGACCAGU-GUUUC$N^{61}$  (formula 2) (SEQ ID NO:20)

$N^1$GGAUACUAGGGCAUUA-AUGUUACCAGUGUAGUC$N^{62}$ (formula 3) (SEQ ID NO:21).

4. The aptamer according to claim 1, comprising the nucleotide sequence of SEQ ID NO: 2 or 7.

5. The aptamer according to claim 1, comprising the nucleotide sequence of SEQ ID NO: 1, 3, 4, 5, 6, 8, 10 or 11.

6. The aptamer according to claim 1, which has a nucleotide length of not more than 45.

7. The aptamer according to claim 1, wherein at least one nucleotide is modified.

8. A complex comprising the aptamer according to claim 1 and a functional substance.

9. The complex according to claim 8, wherein the functional substance is an affinity substance, a labeling substance, an enzyme, a drug delivery vehicle or a drug.

10. A medicament comprising the aptamer according to claim 1 or a complex comprising the aptamer according to claim 1 and a functional substance.

11. A method for the treatment or prophylaxis of a disease accompanied by angiogenesis, bone-articular disease or pain, comprising administering an effective amount of the aptamer according to claim 1 or a complex comprising the aptamer according to claim 1 and a functional substance to a subject.

* * * * *